(12) United States Patent
Rinberg et al.

(10) Patent No.: US 10,041,935 B2
(45) Date of Patent: Aug. 7, 2018

(54) IDENTIFICATION OF OLFACTORY RECEPTORS SENSITIVE TO DIFFERENT ODORANTS

(71) Applicants: New York University, New York, NY (US); Howard Hughes Medical Institute, Chevy Chase, MD (US)

(72) Inventors: Dmitry Rinberg, New York, NY (US); Eric R. Schreiter, Ashburn, VA (US); Loren L. Looger, Sterling, VA (US); Benjamin F. Fosque, Arlington, VA (US)

(73) Assignees: New York University, New York, NY (US); Howard Hughes Medical Institute, Chevy Chase, MD (US)

( * ) Notice: Subject to any disclaimer, the term of this patent is extended or adjusted under 35 U.S.C. 154(b) by 518 days.

(21) Appl. No.: 14/451,998

(22) Filed: Aug. 5, 2014

(65) Prior Publication Data
US 2015/0038338 A1 Feb. 5, 2015

Related U.S. Application Data

(60) Provisional application No. 61/862,296, filed on Aug. 5, 2013.

(51) Int. Cl.
*G01N 33/50* (2006.01)
*G01N 33/68* (2006.01)
*G01N 33/58* (2006.01)

(52) U.S. Cl.
CPC ....... *G01N 33/5058* (2013.01); *G01N 33/582* (2013.01); *G01N 2333/705* (2013.01)

(58) Field of Classification Search
None
See application file for complete search history.

(56) References Cited

U.S. PATENT DOCUMENTS 8,298,781 B2 10/2012 Matsunami et al.

FOREIGN PATENT DOCUMENTS

WO 2002059349 8/2002
WO 2006002161 1/2006

OTHER PUBLICATIONS

Wiedenmann, J., et al., EosFP, a fluorescent marker protein with UV-inducible green-to-red fluorescence conversion, Proc. Natl. Acad. Sci., Nov. 9, 2004, vol. 101, No. 45, pp. 15905-15910.
Ando, R., et al., An optical marker based on the UV-induced green-to-red photoconversion of a fluorescent protein, Proc. Natl. Acad. Sci., Oct. 1, 2002, vol. 99, No. 20, pp. 12651-12656.
Baird, G.S., et al., Circular permutation and receptor insertion within green fluorescent proteins, Proc. Natl. Acad. Sci., Jul. 26, 1999, vol. 96, pp. 11241-11246.
McKinney, S.A., et al., A bright and photostable photoconvertible fluorescent protein for fusion tags, Nat. Methods., Feb. 2009, vol. 6, No. 2, pp. 131-133.
Akerboom, J., et al., Optimization of a GCaMP calcium indicator for neural activity imaging, J. Neurosci. Oct. 3, 2012, vol. 32, No. 40, pp. 13819-13840.
Thorn, P., Ca2+ influx during agonist and Ins(2,4,5)P3-evoked Ca2+ oscillations in HeLa epithelial cells, J. Physiol. 1995, vol. 482, Pt. 2, pp. 275-281.
Uozumi et al., In vivo imaging of Ras protein's activity in olfactory neurons, Protocol Exchange, Feb. 6, 2013, 5 pages.
Touhara et al., Functional identification and reconstitution of an ordorant receptor in single olfactory neurons, Proc. Natl. Acad. Sci. USA, vol. 96, pp. 4040-4045, Mar. 1999.
Kajiya et al., Molecular Bases of Odor Discrimination: Reconstitution of Olfactory Receptors that Recognize Overlapping Sets of Odorants, The Journal of Neuroscience, 21(16):6018-6025.

*Primary Examiner* — John D Ulm
(74) *Attorney, Agent, or Firm* — Hodgson Russ LLP

(57) ABSTRACT

This disclosure provides methods for identification of olfactory sensosry neurons (OSN) that recognize specific odorants. The method comprises introducing into the OSN, a permanent activity marker which exhibits a detectable and permanent change upon activation of the neuron in response to an odorant and exposure to an exteranal stimulus, such as light. The OSN can be isolated and its receptor characterized.

13 Claims, 22 Drawing Sheets
(21 of 22 Drawing Sheet(s) Filed in Color)

Figure 4  CaMPARI v0.1

Figure 6    CaMPARI v1

SEQUENCE LISTING

<160> NUMBER OF SEQ ID NOS: 16

<210> SEQ ID NO 1
<211> LENGTH: 435
<212> TYPE: PRT
<213> ORGANISM: Artificial Sequence
<220> FEATURE:
<223> OTHER INFORMATION: synthetic CaMPARI protein

<400> SEQUENCE: 1

Met Leu Gln Asn Glu Leu Ala Leu Lys Leu Ala Gly Leu Asp Ile Asn
1               5                   10                  15

Lys Thr Gly Gly Ser His His His His His Gly Ser Asp Gln Leu
            20                  25                  30

Thr Glu Glu Gln Ile Ala Glu Phe Lys Glu Ala Phe Ser Leu Phe Asp
        35                  40                  45

Lys Asp Gly Asp Gly Thr Ile Thr Thr Lys Glu Leu Gly Thr Val Met
50                  55                  60

Arg Ser Leu Gly Gln Asn Pro Thr Glu Ala Glu Leu Gln Asp Met Ile
65                  70                  75                  80

Asn Glu Val Asp Ala Asp Gly Asp Gly Thr Ile Asp Phe Pro Glu Phe
                85                  90                  95

Leu Thr Met Met Ala Arg Lys Met Lys Asp Thr Asp Ser Glu Glu Glu
            100                 105                 110

Ile Arg Glu Ala Phe Arg Val Phe Asp Lys Asp Gly Asn Gly Tyr Ile
        115                 120                 125

Ser Ala Ala Glu Leu Arg His Val Met Thr Asn Leu Gly Glu Lys Leu
130                 135                 140

Thr Asp Glu Glu Val Asp Glu Met Ile Arg Glu Ala Asp Ile Asp Gly
145                 150                 155                 160

Asp Gly Gln Val Asn Tyr Glu Glu Phe Val Gln Met Met Thr Ala Lys
                165                 170                 175

Leu Glu Cys Glu Lys Ile Tyr Val Arg Asp Gly Val Leu Thr Gly Asp
            180                 185                 190

Ile His Met Ile Leu Leu Leu Glu Gly Asn Ala His Tyr Arg Cys Asp
        195                 200                 205

Phe Arg Thr Thr Tyr Lys Ala Lys Glu Lys Gly Val Lys Leu Pro Gly
210                 215                 220

Val His Phe Val Asp His Cys Ile Glu Ile Leu Ser His Asp Lys Asp
225                 230                 235                 240

Tyr Asn Lys Val Lys Leu Tyr Glu Tyr Ala Val Ala His Ser Gly Leu
                245                 250                 255

Pro Asp Asn Ala Arg Arg Gly Gly Thr Gly Gly Ser Met Val Ser Ala
            260                 265                 270

Ile Lys Pro Asp Met Lys Ile Lys Leu Arg Met Glu Gly Asn Val Asn
        275                 280                 285

Gly His His Phe Val Ile Asp Gly Asp Gly Thr Gly Lys Pro Tyr Glu
290                 295                 300

Gly Lys Gln Thr Met Asp Leu Glu Val Lys Glu Gly Gly Pro Leu Pro
305                 310                 315                 320

Phe Ala Phe Asp Ile Leu Thr Thr Ala Phe His Tyr Gly Asn Arg Val
                325                 330                 335

Phe Val Lys Tyr Pro Asp Asn Ile Gln Asp Tyr Phe Lys Gln Ser Phe
            340                 345                 350

```
Pro Lys Gly Tyr Ser Trp Glu Arg Ser Met Thr Phe Glu Asp Gly Gly
        355                 360                 365

Ile Cys Tyr Ala Arg Asn Asp Ile Thr Met Glu Gly Asp Thr Phe Tyr
    370                 375                 380

Asn Lys Val Arg Phe Tyr Gly Thr Asn Phe Pro Ala Asn Gly Pro Val
385                 390                 395                 400

Met Gln Lys Lys Thr Leu Lys Trp Met Pro Ser Trp Thr Arg Ser Ser
                405                 410                 415

Arg Arg Lys Trp Asn Lys Thr Gly His Ala Val Arg Ala Ile Gly Arg
                420                 425                 430

Leu Ser Ser
        435

<210> SEQ ID NO 2
<211> LENGTH: 84
<212> TYPE: PRT
<213> ORGANISM: Artificial Sequence
<220> FEATURE:
<223> OTHER INFORMATION: synthetic CaMPARI protein

<400> SEQUENCE: 2

Cys Glu Lys Ile Tyr Val Arg Asp Gly Val Leu Thr Gly Asp Ile His
1               5                   10                  15

Met Ile Leu Leu Leu Glu Gly Asn Ala His Tyr Arg Cys Asp Phe Arg
            20                  25                  30

Thr Thr Tyr Lys Ala Lys Glu Lys Gly Val Lys Leu Pro Gly Val His
        35                  40                  45

Phe Val Asp His Cys Ile Glu Ile Leu Ser His Asp Lys Asp Tyr Asn
    50                  55                  60

Lys Val Lys Leu Tyr Glu Tyr Ala Val Ala His Ser Gly Leu Pro Asp
65                  70                  75                  80

Asn Ala Arg Arg

<210> SEQ ID NO 3
<211> LENGTH: 144
<212> TYPE: PRT
<213> ORGANISM: Artificial Sequence
<220> FEATURE:
<223> OTHER INFORMATION: synthetic CaMPARI protein

<400> SEQUENCE: 3

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe His Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Asn Asp Ile Thr Met Glu Gly
                100                 105                 110

Asp Thr Phe Tyr Asn Lys Val Arg Phe Tyr Gly Thr Asn Phe Pro Ala
            115                 120                 125
```

```
Asn Gly Pro Val Met Gln Lys Lys Thr Leu Lys Trp Met Pro Ser Trp
        130                 135                 140

<210> SEQ ID NO 4
<211> LENGTH: 147
<212> TYPE: PRT
<213> ORGANISM: Artificial Sequence
<220> FEATURE:
<223> OTHER INFORMATION: synthetic CaMPARI protein

<400> SEQUENCE: 4

Asp Gln Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Met Arg Ser Leu Gly Gln Asn Pro Thr Glu Ala Glu Leu Gln
        35                  40                  45

Asp Met Ile Asn Glu Val Asp Ala Asp Gly Asp Gly Thr Ile Asp Phe
    50                  55                  60

Pro Glu Phe Leu Thr Met Met Ala Arg Lys Met Lys Asp Thr Asp Ser
65                  70                  75                  80

Glu Glu Glu Ile Arg Glu Ala Phe Arg Val Phe Asp Lys Asp Gly Asn
                85                  90                  95

Gly Tyr Ile Ser Ala Ala Glu Leu Arg His Val Met Thr Asn Leu Gly
            100                 105                 110

Glu Lys Leu Thr Asp Glu Glu Val Asp Glu Met Ile Arg Glu Ala Asp
        115                 120                 125

Ile Asp Gly Asp Gly Gln Val Asn Tyr Glu Glu Phe Val Gln Met Met
    130                 135                 140

Thr Ala Lys
145

<210> SEQ ID NO 5
<211> LENGTH: 21
<212> TYPE: PRT
<213> ORGANISM: Artificial Sequence
<220> FEATURE:
<223> OTHER INFORMATION: synthetic CaMPARI protein

<400> SEQUENCE: 5

Ser Ser Arg Arg Lys Trp Asn Lys Thr Gly His Ala Val Arg Ala Ile
1               5                   10                  15

Gly Arg Leu Ser Ser
            20

<210> SEQ ID NO 6
<211> LENGTH: 19
<212> TYPE: PRT
<213> ORGANISM: Artificial Sequence
<220> FEATURE:
<223> OTHER INFORMATION: synthetic CaMPARI protein

<400> SEQUENCE: 6

Met Leu Gln Asn Glu Leu Ala Leu Lys Leu Ala Gly Leu Asp Ile Asn
1               5                   10                  15

Lys Thr Gly

<210> SEQ ID NO 7
<211> LENGTH: 1308
<212> TYPE: DNA
```

<213> ORGANISM: Artificial Sequence
<220> FEATURE:
<223> OTHER INFORMATION: DNA encoding synthetic CaMAPRI protein

<400> SEQUENCE: 7

```
atgctgcaga acgagcttgc tcttaagttg gctggacttg atattaacaa gactggaggt      60
tctcatcatc accaccacca tggatccgac caactgactg aagagcagat cgcagaattt     120
aaagaggctt ctccctatt tgacaaggac ggggatggga caataacaac caaggagctg      180
gggacggtga tgcggtctct ggggcagaac cccacagaag cagagctgca ggacatgatc     240
aatgaagtag atgccgacgg tgacggcaca atcgacttcc ctgagttcct gacaatgatg     300
gcaagaaaaa tgaaagacac agacagtgaa gaagaaatta gagaagcgtt ccgtgtgttt     360
gataaggatg gcaatggcta catcagtgca gcagagcttc gccacgtgat gacaaacctt     420
ggagagaagt taacagatga agaggttgat gaaatgatca gggaagcaga catcgatggg     480
gatggtcagg taaactacga agagtttgta caaatgatga cagcgaagct cgagtgcgag     540
aaaatctatg tgcgtgatgg agtgctgacg ggtgatattc atatgatctt gttgcttgaa     600
ggaaatgccc attaccgatg tgacttcaga actacttaca aagctaagga agggtgtc      660
aagttaccag gcgtgcactt tgtggaccac tgcattgaga ttttaagcca tgacaaagat     720
tacaacaagg ttaagctgta tgagtatgct gttgctcatt ctggattgcc tgacaatgcc     780
agacgaggcg gtaccggcgg atccatggtg agtgcgatta gccagacat gaagatcaaa      840
ctccgtatgg aaggcaacgt aaacgggcac cactttgtga tcgacggaga tggtacaggc     900
aagccttatg agggaaaaca gaccatggat cttgaagtca aagagggcgg acctctgcct     960
tttgcctttg atatcctgac cactgcattc cattacggca acagggtatt cgtgaaatat    1020
ccagacaaca tacaagacta ttttaagcag tcgtttccta agggtattc gtgggaacga     1080
agcatgactt tcgaagacgg gggcatttgc tatgccagaa acgacataac aatggaaggg    1140
gacactttct ataataaagt tcgattttat ggtaccaact ttcccgccaa tggtccagtt    1200
atgcagaaga agacgctgaa atggatgccg agctggacgc gttcatcacg tcgtaagtgg    1260
aataagacag gtcacgcagt cagagctata ggtcggctga gctcataa              1308
```

<210> SEQ ID NO 8
<211> LENGTH: 415
<212> TYPE: PRT
<213> ORGANISM: Artificial Sequence
<220> FEATURE:
<223> OTHER INFORMATION: Synthetic protein

<400> SEQUENCE: 8

```
Met His His His His His His Gly Ser Ser Arg Arg Lys Trp Asn
1               5                   10                  15

Lys Thr Gly His Ala Val Arg Ala Ile Gly Arg Leu Ser Ser Leu Glu
            20                  25                  30

Gly Glu Lys Met Tyr Val Arg Asp Gly Val Leu Thr Gly Asp Ile His
        35                  40                  45

Met Ala Leu Leu Leu Glu Gly Asn Ala His Tyr Arg Cys Asp Phe Arg
    50                  55                  60

Thr Thr Tyr Lys Ala Lys Glu Lys Gly Val Lys Leu Pro Gly Tyr His
65                  70                  75                  80

Phe Val Asp His Cys Ile Glu Ile Leu Ser His Asp Lys Asp Tyr Asn
                85                  90                  95

Lys Val Lys Leu Tyr Glu His Ala Val Ala His Ser Gly Leu Pro Asp
```

```
            100                 105                 110
Asn Ala Arg Arg Gly Thr Gly Gly Ser Met Val Ser Ala Ile Lys
        115                 120                 125

Pro Asp Met Lys Ile Lys Leu Arg Met Glu Gly Asn Val Asn Gly His
        130                 135                 140

His Phe Val Ile Asp Gly Asp Gly Thr Gly Lys Pro Tyr Glu Gly Lys
145                 150                 155                 160

Gln Thr Met Asp Leu Glu Val Lys Glu Gly Gly Pro Leu Pro Phe Ala
                165                 170                 175

Phe Asp Ile Leu Thr Thr Ala Phe His Tyr Gly Asn Arg Val Phe Val
            180                 185                 190

Lys Tyr Pro Asp Asn Ile Gln Asp Tyr Phe Lys Gln Ser Phe Pro Lys
        195                 200                 205

Gly Tyr Ser Trp Glu Arg Ser Leu Thr Phe Glu Asp Gly Gly Ile Cys
        210                 215                 220

Tyr Ala Arg Asn Asp Ile Thr Met Glu Gly Asp Thr Phe Tyr Asn Lys
225                 230                 235                 240

Val Arg Phe Tyr Gly Thr Asn Phe Pro Ala Asn Gly Pro Val Met Gln
                245                 250                 255

Lys Lys Thr Leu Lys Trp Glu Pro Ser Thr Thr Arg Asp Gln Leu Thr
            260                 265                 270

Glu Glu Gln Ile Ala Glu Phe Lys Glu Ala Phe Ser Leu Phe Asp Lys
        275                 280                 285

Asp Gly Asp Gly Thr Ile Thr Thr Lys Glu Leu Gly Thr Val Met Arg
        290                 295                 300

Ser Leu Gly Gln Asn Pro Thr Glu Ala Glu Leu Gln Asp Met Ile Asn
305                 310                 315                 320

Glu Val Asp Ala Asp Gly Asp Gly Thr Ile Asp Phe Pro Glu Phe Leu
                325                 330                 335

Thr Met Met Ala Arg Lys Met Lys Asp Thr Asp Ser Glu Glu Glu Ile
            340                 345                 350

Arg Glu Ala Phe Arg Val Phe Asp Lys Asp Gly Asn Gly Tyr Ile Ser
        355                 360                 365

Ala Ala Glu Leu Arg His Val Met Thr Asn Leu Gly Glu Lys Leu Thr
        370                 375                 380

Asp Glu Glu Val Asp Glu Met Ile Arg Glu Ala Asp Ile Asp Gly Asp
385                 390                 395                 400

Gly Gln Val Asn Tyr Glu Glu Phe Val Gln Met Met Thr Ala Lys
                405                 410                 415

<210> SEQ ID NO 9
<211> LENGTH: 1248
<212> TYPE: DNA
<213> ORGANISM: Artificial Sequence
<220> FEATURE:
<223> OTHER INFORMATION: DNA encoding synthetic protein

<400> SEQUENCE: 9
atgcatcatc accaccacca tggatcctca tcacgtcgta agtggaataa gacaggtcac      60
gcagtcagag ctataggtcg gctgagctca ctcgagggcg agaaaatgta tgtgcgtgat     120
ggagtgctga cgggtgatat tcatatggct ttgttgcttg aaggaaatgc ccattaccga     180
tgtgacttca gaactactta caaagctaag gagaagggtg tcaagttacc aggctaccac     240
tttgtggacc actgcattga gattttaagc catgacaaag attacaacaa ggttaagctg     300
```

-continued

```
tatgagcatg ctgttgctca ttctggattg cctgacaatg ccagacgagg cggtaccgga    360
gggagcatgg tgagtgcgat taagccagac atgaagatca aactccgtat ggaaggcaac    420
gtaaacgggc accactttgt gatcgacgga gatggtacag gcaagcctta tgagggaaaa    480
cagaccatga tcttgaagt caaagagggc ggacctctgc cttttgcctt tgatatcctg    540
accactgcat tccattacgg caacagggta ttcgtgaaat atccagacaa catacaagac    600
tattttaagc agtcgtttcc taaggggtat tcgtgggaac gaagcttgac tttcgaagac    660
gggggcattt gctatgccag aaacgacata acaatggaag gggacacttt ctataataaa    720
gttcgatttt atggtaccaa ctttcccgcc aatggtccag ttatgcagaa gaagacgctg    780
aaatgggagc cctccaccac gcgtgaccaa ctgactgaag agcagatcgc agaatttaaa    840
gaggctttct ccctatttga caaggacggg gatgggacaa taacaaccaa ggagctgggg    900
acggtgatgc ggtctctggg gcagaacccc acagaagcag agctgcagga catgatcaat    960
gaagtagatg ccgacggtga cggcacaatc gacttccctg agttcctgac aatgatggca    1020
agaaaaatga agacacaga cagtgaagaa gaaattagag aagcgttccg tgtgtttgat    1080
aaggatggca atggctacat cagtgcagca gagcttcgcc acgtgatgac aaaccttgga    1140
gagaagttaa cagatgaaga ggttgatgaa atgatcaggg aagcagacat cgatggggat    1200
ggtcaggtaa actacgaaga gtttgtacaa atgatgacag cgaagtaa                 1248
```

<210> SEQ ID NO 10
<211> LENGTH: 414
<212> TYPE: PRT
<213> ORGANISM: Artificial Sequence
<220> FEATURE:
<223> OTHER INFORMATION: Synthetic protein

<400> SEQUENCE: 10

```
Met His His His His His Gly Ser Ser Arg Arg Lys Trp Asn
1               5                   10                  15

Lys Thr Gly His Ala Val Arg Ala Ile Gly Arg Leu Ser Ser Leu Glu
            20                  25                  30

Arg Met Ala Leu Leu Leu Glu Gly Asn Ala His Tyr Arg Cys Asp Phe
        35                  40                  45

Arg Thr Thr Tyr Lys Ala Lys Glu Lys Gly Val Lys Leu Pro Gly Tyr
    50                  55                  60

His Phe Val Asp His Cys Ile Glu Ile Leu Ser His Asp Lys Asp Tyr
65                  70                  75                  80

Asn Lys Val Lys Leu Tyr Glu His Ala Val Ala His Ser Gly Leu Pro
                85                  90                  95

Asp Asn Ala Arg Arg Gly Gly Thr Gly Gly Ser Met Val Ser Ala Ile
            100                 105                 110

Lys Pro Asp Met Lys Ile Lys Leu Arg Met Glu Gly Asn Val Asn Gly
        115                 120                 125

His His Phe Val Ile Asp Gly Asp Gly Thr Gly Lys Pro Tyr Glu Gly
    130                 135                 140

Lys Gln Thr Met Asp Leu Glu Val Lys Glu Gly Gly Pro Leu Pro Phe
145                 150                 155                 160

Ala Phe Asp Ile Leu Thr Thr Ala Phe His Tyr Gly Asn Arg Val Phe
                165                 170                 175

Val Lys Tyr Pro Asp Asn Ile Gln Asp Tyr Phe Lys Gln Ser Phe Pro
            180                 185                 190

Lys Gly Tyr Ser Trp Glu Arg Ser Met Thr Phe Glu Asp Gly Gly Ile
```

```
            195                 200                 205
Cys Tyr Ala Arg Asn Asp Ile Thr Met Glu Gly Asp Thr Phe Tyr Asn
    210                 215                 220

Lys Val Arg Phe Tyr Gly Thr Asn Phe Pro Ala Asn Gly Pro Val Met
225                 230                 235                 240

Gln Lys Lys Thr Leu Lys Trp Glu Pro Ser Thr Glu Lys Met Tyr Val
                245                 250                 255

Arg Asp Gly Val Leu Thr Gly Asp Ser Thr Arg Asp Gln Leu Thr Glu
            260                 265                 270

Glu Gln Ile Ala Glu Phe Lys Glu Ala Phe Ser Leu Phe Asp Lys Asp
        275                 280                 285

Gly Asp Gly Thr Ile Thr Thr Lys Glu Leu Gly Thr Val Met Arg Ser
    290                 295                 300

Leu Gly Gln Asn Pro Thr Glu Ala Glu Leu Gln Asp Met Ile Asn Glu
305                 310                 315                 320

Val Asp Ala Asp Gly Asp Gly Thr Ile Asp Phe Pro Glu Phe Leu Thr
                325                 330                 335

Met Met Ala Arg Lys Met Lys Asp Thr Asp Ser Glu Glu Glu Ile Arg
            340                 345                 350

Glu Ala Phe Arg Val Phe Asp Lys Asp Gly Asn Gly Tyr Ile Ser Ala
        355                 360                 365

Ala Glu Leu Arg His Val Met Thr Asn Leu Gly Glu Lys Leu Thr Asp
    370                 375                 380

Glu Glu Val Asp Glu Met Ile Arg Glu Ala Asp Ile Asp Gly Asp Gly
385                 390                 395                 400

Gln Val Asn Tyr Glu Glu Phe Val Gln Met Met Thr Ala Lys
                405                 410

<210> SEQ ID NO 11
<211> LENGTH: 1245
<212> TYPE: DNA
<213> ORGANISM: Artificial Sequence
<220> FEATURE:
<223> OTHER INFORMATION: DNA encoding synthetic protein

<400> SEQUENCE: 11
atgcatcatc accaccacca tggatcctca tcacgtcgta agtggaataa gacaggtcac      60
gcagtcagag ctataggtcg gctgagctca ctcgagcgga tggcgttgtt gcttgaagga     120
aatgcccatt accgatgtga cttcagaact acttacaaag ctaaggagaa gggtgtcaag     180
ttaccaggct accactttgt ggaccactgc attgagattt taagccatga caaagattac     240
aacaaggtta agctgtatga gcatgctgtt gctcattctg gattgcctga caatgccaga     300
cgaggcggta ccggcggatc catggtgagt gcgattaagc cagacatgaa gatcaaactc     360
cgtatggaag gcaacgtaaa cgggcaccac tttgtgatcg acggagatgg tacaggcaag     420
ccttatgagg gaaaacagac catggatctt gaagtcaaag agggcggacc tctgccttt     480 gcctttgata tcctgaccac tgcattccat tacggcaaca gggtattcgt gaaatatcca     540
gacaacatac aagactattt taagcagtcg tttcctaagg ggtattcgtg gaacgaagc     600 atgactttcg aagacggggg catttgctat gccagaaacg atataacaat ggaagggac     660 actttctata ataaagttcg attttatggt accaactttc ccgccaatgg tccagttatg     720
cagaagaaga cgctgaaatg ggagccctcc actgagaaaa tgtatgtgcg tgatggagtg     780
ctgacgggtg actccacgcg tgaccaactg actgaagagc agatcgcaga atttaaagag     840
```

-continued

```
gctttctccc tatttgacaa ggacggggat gggacaataa caaccaagga gctggggacg    900
gtgatgcggt ctctggggca gaaccccaca gaagcagagc tgcaggacat gatcaatgaa    960
gtagatgccg acggtgacgg cacaatcgac ttccctgagt tcctgacaat gatggcaaga   1020
aaaatgaaag acacagacag tgaagaagaa attagagaag cgttccgtgt gtttgataag   1080
gatggcaatg gctacatcag tgcagcagag cttcgccacg tgatgacaaa ccttggagag   1140
aagttaacag atgaagaggt tgatgaaatg atcagggaag cagacatcga tggggatggt   1200
caggtaaact acgaagagtt tgtacaaatg atgacagcga agtaa                   1245
```

<210> SEQ ID NO 12
<211> LENGTH: 19
<212> TYPE: PRT
<213> ORGANISM: Artificial Sequence
<220> FEATURE:
<223> OTHER INFORMATION: synthetic peptide signal sequence

<400> SEQUENCE: 12

Met Leu Gln Asn Glu Leu Ala Leu Lys Leu Ala Gly Leu Asp Ile Asn
1               5                   10                  15

Lys Thr Gly

<210> SEQ ID NO 13
<211> LENGTH: 226
<212> TYPE: PRT
<213> ORGANISM: Artificial Sequence
<220> FEATURE:
<223> OTHER INFORMATION: Synthetic protein

<400> SEQUENCE: 13

Met Ser Ala Ile Lys Pro Asp Met Lys Ile Lys Leu Arg Met Glu Gly
1               5                   10                  15

Asn Val Asn Gly His His Phe Val Ile Asp Gly Asp Gly Thr Gly Lys
                20                  25                  30

Pro Phe Glu Gly Lys Gln Ser Met Asp Leu Glu Val Lys Glu Gly Gly
            35                  40                  45

Pro Leu Pro Phe Ala Phe Asp Ile Leu Thr Thr Ala Phe His Tyr Gly
        50                  55                  60

Asn Arg Val Phe Ala Lys Tyr Pro Asp Asn Ile Gln Asp Tyr Phe Lys
65                  70                  75                  80

Gln Ser Phe Pro Lys Gly Tyr Ser Trp Glu Arg Ser Leu Thr Phe Glu
                85                  90                  95

Asp Gly Gly Ile Cys Ile Ala Arg Asn Asp Ile Thr Met Glu Gly Asp
            100                 105                 110

Thr Phe Tyr Asn Lys Val Arg Phe Tyr Gly Thr Asn Phe Pro Ala Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Thr Gly Asp Ile His Met Ala
145                 150                 155                 160

Leu Leu Leu Glu Gly Asn Ala His Tyr Arg Cys Asp Phe Arg Thr Thr
                165                 170                 175

Tyr Lys Ala Lys Glu Lys Gly Val Lys Leu Pro Gly Tyr His Phe Val
            180                 185                 190

Asp His Cys Ile Glu Ile Leu Ser His Asp Lys Asp Tyr Asn Lys Val
        195                 200                 205

Lys Leu Tyr Glu His Ala Val Ala His Ser Gly Leu Pro Asp Asn Ala

Arg Arg
225

<210> SEQ ID NO 14
<211> LENGTH: 415
<212> TYPE: PRT
<213> ORGANISM: Artificial Sequence
<220> FEATURE:
<223> OTHER INFORMATION: Synthetic protein

<400> SEQUENCE: 14

Met His His His His His Gly Ser Asp Gln Leu Thr Glu Glu Gln
1               5                   10                  15

Ile Ala Glu Phe Lys Glu Ala Phe Ser Leu Phe Asp Lys Asp Gly Asp
            20                  25                  30

Gly Thr Ile Thr Thr Lys Glu Leu Gly Thr Val Met Arg Ser Leu Gly
        35                  40                  45

Gln Asn Pro Thr Glu Ala Glu Leu Gln Asp Met Ile Asn Glu Val Asp
    50                  55                  60

Ala Asp Gly Asp Gly Thr Ile Asp Phe Pro Glu Phe Leu Thr Met Met
65                  70                  75                  80

Ala Arg Lys Met Lys Asp Thr Asp Ser Glu Glu Glu Ile Arg Glu Ala
                85                  90                  95

Phe Arg Val Phe Asp Lys Asp Gly Asn Gly Tyr Ile Ser Ala Ala Glu
            100                 105                 110

Leu Arg His Val Met Thr Asn Leu Gly Glu Lys Leu Thr Asp Glu Glu
        115                 120                 125

Val Asp Glu Met Ile Arg Glu Ala Asp Ile Asp Gly Asp Gly Gln Val
    130                 135                 140

Asn Tyr Glu Glu Phe Val Gln Met Met Thr Ala Lys Leu Glu Cys Glu
145                 150                 155                 160

Lys Met Tyr Val Arg Asp Gly Val Leu Thr Gly Asp Ile His Met Ala
                165                 170                 175

Leu Leu Leu Glu Gly Asn Ala His Tyr Arg Cys Asp Phe Arg Thr Thr
            180                 185                 190

Tyr Lys Ala Lys Glu Lys Gly Val Lys Leu Pro Gly Tyr His Phe Val
        195                 200                 205

Asp His Cys Ile Glu Ile Leu Ser His Asp Lys Asp Tyr Asn Lys Val
    210                 215                 220

Lys Leu Tyr Glu His Ala Val Ala His Ser Gly Leu Pro Asp Asn Ala
225                 230                 235                 240

Arg Arg Gly Gly Thr Gly Gly Ser Met Val Ser Ala Ile Lys Pro Asp
                245                 250                 255

Met Lys Ile Lys Leu Arg Met Glu Gly Asn Val Asn Gly His His Phe
            260                 265                 270

Val Ile Asp Gly Asp Gly Thr Gly Lys Pro Tyr Glu Gly Lys Gln Thr
        275                 280                 285

Met Asp Leu Glu Val Lys Glu Gly Gly Pro Leu Pro Phe Ala Phe Asp
    290                 295                 300

Ile Leu Thr Thr Ala Phe His Tyr Gly Asn Arg Val Phe Val Lys Tyr
305                 310                 315                 320

Pro Asp Asn Ile Gln Asp Tyr Phe Lys Gln Ser Phe Pro Lys Gly Tyr
                325                 330                 335

Ser Trp Glu Arg Ser Met Thr Phe Glu Asp Gly Gly Ile Cys Tyr Ala

```
                    340              345              350
Arg Asn Asp Ile Thr Met Glu Gly Asp Thr Phe Tyr Asn Lys Val Arg
                355                       360                   365

Phe Tyr Gly Thr Asn Phe Pro Ala Asn Gly Pro Val Met Gln Lys Lys
        370                       375                   380

Thr Leu Lys Trp Glu Pro Ser Trp Thr Arg Ser Arg Arg Lys Trp
385                       390                   395                   400

Asn Lys Thr Gly His Ala Val Arg Ala Ile Gly Arg Leu Ser Ser
                405                       410                   415

<210> SEQ ID NO 15
<211> LENGTH: 1248
<212> TYPE: DNA
<213> ORGANISM: Artificial Sequence
<220> FEATURE:
<223> OTHER INFORMATION: DNA encoding v0.1 protein

<400> SEQUENCE: 15
atgcatcatc accaccacca tggatccgac caactgactg aagagcagat cgcagaattt      60
aaagaggctt tctccctatt tgacaaggac ggggatggga caataacaac caaggagctg    120
gggacggtga tgcggtctct ggggcagaac cccacagaag cagagctgca ggacatgatc    180
aatgaagtag atgccgacgg tgacggcaca atcgacttcc ctgagttcct gacaatgatg    240
gcaagaaaaa tgaaagacac agacagtgaa gaagaaatta gaagcgttc cgtgtgtttt     300 gataaggatg gcaatggcta catcagtgca gcagagcttc gccacgtgat gacaaacctt    360
ggagagaagt taacagatga gaggttgat gaaatgatca gggaagcaga catcgatggg     420
gatggtcagg taaactacga agagtttgta caaatgatga cagcgaagct cgagtgcgag    480
aaaatgtatg tgcgtgatgg agtgctgacg ggtgatattc atatggcttt gttgcttgaa    540
ggaaatgccc attaccgatg tgacttcaga actacttaca agctaagga agggtgtc      600 aagttaccag ctaccactt tgtggaccac tgcattgaga ttttaagcca tgacaaagat    660
tacaacaagg ttaagctgta tgagcatgct gttgctcatt ctggattgcc tgacaatgcc    720
agacgaggcg gtaccggcgg atccatggtg agtgcgatta gccagacat gaagatcaaa     780 ctccgtatgg aaggcaacgt aaacgggcac cactttgtga tcgacggaga tggtacaggc    840
aagccttatg agggaaaaca gaccatggat cttgaagtca agagggcgga acctctgcct    900 tttgccttg atatcctgac cactgcattc cattacggca cagggtatt cgtgaaatat       960 ccagacaaca tacaagacta ttttaagcag tcgtttccta aggggtattc gtgggaacga    1020
agcatgactt tcgaagacgg gggcattgc tatgccagaa acgacataac aatggaaggg    1080
gacactttct ataataaagt tcgattttat ggtaccaact ttcccgccaa tggtccagtt    1140
atgcagaaga agacgctgaa atgggaacca agctggacgc gttcatcacg tcgtaagtgg    1200
aataagacag gtcacgcagt cagagctata ggtcggctga gctcataa                 1248

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide linker

<400> SEQUENCE: 16

Gly Gly Thr Gly Gly Ser
1               5
```

IDENTIFICATION OF OLFACTORY RECEPTORS SENSITIVE TO DIFFERENT ODORANTS

REFERENCE TO RELATED APPLICATIONS

This application claims priority to U.S. Provisional application No. 61/862,296, filed on Aug. 5, 2013, the disclosure of which is incorporated by reference in its entirety.

BACKGROUND OF THE INVENTION

Humans sense odorants in the environment via a large number of olfactory sensory neurons (OSNs) in the olfactory epithelium in the nose. Each OSN expresses only one olfactory receptor (OR) gene out of a large family of OR genes (~350 in humans and ~1200 in mice). OSNs project their axon to the olfactory bulb (OB) in the brain and all OSNs that express the same OR gene converge to one or a few areas in OB, called glomeruli. Individual odorants can excite multiple types of OR, and each OR can be excited by multiple odorants. Thus, coding of odorants is combinatorial.

The discovery of OR gene family (Buck & Axel, 1991) opened a new era in olfactory research. Multiple OR genes have been cloned and their properties have been studied systematically. In mice, studies have been carried out by tagging an identified OR gene with a florescent protein (e.g. GFP). OSNs that express a GFP tagged OR gene can be identified in the epithelium, as well as in the corresponding glomerulus in the OB, thus allowing for the study of the response property of this OR. In this way, for a given receptor it is possible to screen a large number of odorants and characterize its molecular receptive range. However, each odorant can excite multiple receptors, and it is very difficult to find all receptors responsive to a given odorant. In addition, it is even more difficult to find which of the receptors responsive to a given odorant are the most sensitive.

Currently it is possible to measure the response of a large population of OSNs in two types of assays: one directed to the epithelium and the other to the OB. In the first assay an odorant is presented to either isolated OSNs or the whole epithelium, and either $Ca^{+2}$ imaging or electrophysiological recordings are used to measure response to this odorant. In the second type of assay, the response is measured in the OB usually by observing $Ca^{+2}$ dynamics in the glomerulus. In both cases, it is difficult to establish genetic identity of OSNs responsive to a specific odorant, i.e., to identify genes of ORs excited by the odorant. An additional shortcoming is that OB imaging usually allows monitoring of only the dorsal area of the OB, which constitutes ~20% of all OB glomeruli.

It would be useful to identify specific ORs for given odorants, however there is no high throughput method for doing this. In addition, it is even more difficult to identify the relative sensitivities of different ORs for a given odorant. The more sensitive receptors may play special role in odor identification.

SUMMARY OF THE INVENTION

Provided are methods and compositions for genetic identification of the receptors (all and the most sensitive) responsive to a given odorant.

In one aspect, this disclosure provides a method for identifying OSNs that recognize a particular odorant comprising the steps of obtaining OSNs into which has been introduced a permanent activity marker (PAM) that can detect when neurons are activated (such as a molecule comprising CaM, EosFP, and M13), exposing the OSNs to the odorant and an external stimulus (such as light), and identifying the OSNs that have a detectable change in the activity of PAM in response to exposure to the odorant and the external stimulus. The OSNs which exhibit a detectable change can be isolated and the OR expressed in such OSNs can be identified. In various embodiments, the PAM molecule may comprise variants of CaM, EosFP and M13 such that the there is a detectable change in the fluorescence of PAM upon activation of the neuron by an odorant. For example, in one embodiment, the fluorescence may change from green to red. The change may be detected as a ratio of red to green fluorescence. The exposure of OSNs may be done in vivo or may be done in isolated OSNs. The isolated OSNs may be in the nasal epithelium or may be isolated cells. The isolated OSNs may be from one individual or may be from different individuals. The method allows creating a record of activation of OSNs in real time in response to odorants.

In one embodiment, the present disclosure provides kits for identification of OSNs that are responsive to specific odorants. The kit comprises a PAM (such as the PAMs disclosed herein), a set odorants comprising one or more odorants, a light source adapted for delivering light to the nasal epithelium, and optionally materials for extraction of the cells and the subsequent identification of ORs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
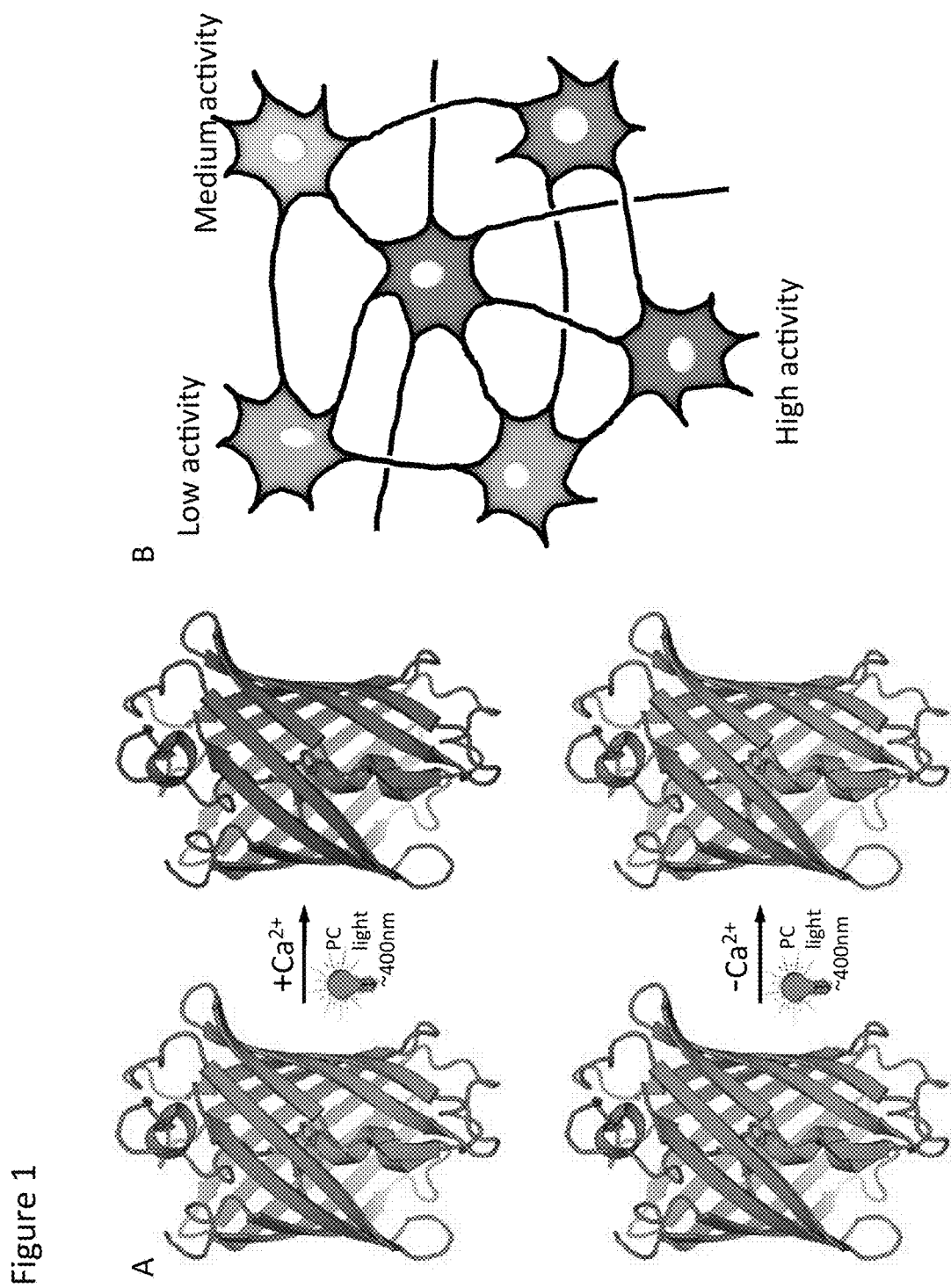
FIG. 1 includes illustrations showing (A) calcium ions accompanying a photoconversion light pulse to effect green-to-red photoconversion of CaMPARI, and (B) neuron cells expressing CaMPARI that have been exposed to a pulse of photoconversion light showing cells that appear more red/darker were more active (higher calcium levels) during the photoconversion pulse, and therefore underwent more green-to-red photoconversion.

An important feature of the present disclosure is obtaining a record (such as based on a permanent change in the cell), of the transient changes in the electrophysiological properties of OSNs, (such as, for example, $Ca^{++}$ levels or voltage levels) in response to odorants. In one embodiment, the record may be a long-lasting record.

In one aspect, the present disclosure provides a method for identification of OSNs in the nasal epithelium that respond to particular odorants.

In another aspect, the present disclosure provides a method for identifying OSNs sensitive to specific odorants and for identifying OR genes that are expressed in these neurons. Since only one OR gene is expressed in an OSN, this embodiment will entail identification of a population of neurons, which respond to the same odorant, but which may contain different OR genes. In one embodiment of this aspect, all OR genes, which correspondent receptors are responsive to an odorant can be identified. In another embodiment of this aspect, the temporal activation of OSNs within an odorant-specific OSN set (i.e., all OSNs that respond to the same odorant, but express different ORs) in response to an odorant can be determined.

The method of the present disclosure comprises introducing a permanent activity marker (PAM) into OSNs. A PAM may be a protein, polypeptide or other small molecule that permanently changes its state after being exposed to external stimulus (such as: electromagnetic radiation including light (including UV light), electro-magnetic field, other chemicals) during an active state of the cell (such as high $Ca^{+2}$, cell depolarization). In one embodiment, the method of the present disclosure comprising introducing a vector encoding a PAM protein into the OSNs of the nasal epithelium and allowing expression of the PAM protein. An example of a PAM is a fluorescent protein, which shifts its florescence wavelength in response to light activation (photo-switching or photo-conversion) only during an epoch of elevated level of $Ca^{++}$ concentration.

Embodiments of PAMs, including but not limited to representative nucleotide sequences, amino acid sequences, cloning procedures, and compositions and methods for making, delivering, and measuring signals from PAMs that are suitable for use with embodiments of the present disclosure are more fully described in the description and figures provided herein. In some non-limiting embodiments, the expression vector can encode a PAM which comprises, consists essentially of, or consists of an Eos fluorescent polypeptide (FP), and modifications thereof as further described herein, a calmodulin (CaM) polypeptide or a variant or a fragment thereof, and an M13 polypeptide, or a variant or a fragment thereof. Modified EosFP polypeptides can include a C-terminus portion comprising the sequence of SEQ ID NO. 2 and an N-terminus portion comprising the sequence of SEQ ID NO. 3, or a variant and/or fragment thereof as set forth in Example A. In some embodiments, the PAM can comprise circularly permuted variants of mEos2 (Nat Methods, February 2009, 6(2): 131-133), and which comprise any of a variety of mutations, including but not necessarily limited to V2ins, F34Y, S39T, A69V, L93M, and I102Y. The sequence of mEOS2 is provided as SEQ ID No. 13. V2ins indicates a valine was inserted at position 2 (i.e., after M and before S). In embodiments, the PAM can comprise one or more circular permutations in a beta strand of an EosFP polypeptide. The PAM can comprise tandem copies of an EosFP, which can be encoded by a vector which has an Eos gene separated by a linker, such as a linker having the sequence GGTGGS (SEQ ID NO:16). In one embodiment, the PAM is referred to as CaMPARI. The PAM and/or a polypeptide comprising a PAM may comprise other components, such as one or more peptide linker domains, purification tags, a nuclear export signal, and the like. In one embodiment, a PAM comprises or has SEQ ID NO: 1.

After introducing the PAM into the OSNs, the OSNs are exposed to an odorant, and those OSNs which express the odorant-specific OR will exhibit an electrophysiological response or $Ca^{++}$ influx, which in turn results in a permanent and detectable change in a property of the PAM upon exposure to an external stimulus. If an OSN exhibits electrophysiological response when exposed to an odorant, it is considered to be activated for the purposes of this disclosure. Activation involves depolarization of cells and influx of calcium. Thus, OSNs that express an OR for which the test odorant is a ligand, exhibit a detectable signal from the PAM upon, or subsequent to, exposure to the test odorant and an external stimulus. The OSNs that were activated by exposure to the odorant can be isolated based on the detectable PAM property, and then the OR receptor gene expressed in the isolated OSNs can be identified thereby correlating the OR with the particular odorant. The identification of any one or a plurality of genes encoding ORs that are reactive to a particular test odorant can be performed using any suitable technique, given the benefit of the present disclosure.

To carry out the method of this invention, a PAM is introduced into the nasal epithelium cells of a test subject. In one embodiment, the test subject may be a human being or a non-human animal. For example, PAM vectors may be introduced in isolated OSNs in culture, OSNs in isolated nasal epithelium or in OSNs in vivo. To culture OSNs, olfactory epithelium can be obtained from the nasal cavity and enzymatically treated (such as with trypsin, chymotrypsin, DNAse and the like) to reduce stroma tissue. Dissociated olfactory sensory neurons can be cultured directly on suitable substrates (such as multi-well clusters, slides, coverslips and the like). If desired, a coating of attachment facilitators such as polylysine, matrigel or a feeder cell layer (such as astrocytes or fibroblasts) can be used to further enhance attachment and survival.

For introduction of PAM encoding sequences into OSNs, a reporter gene under the control of a promoter can be used, wherein the reporter gene encodes for a PAM. An elevation in intracellular Ca++ caused by depolarization of the cell in response to binding of a test odorant to an OR and simultaneous application of external stimulus (like photoconversion light) results in a permanent change in the functionality of PAM such that the change is detectable and can be used as a basis for separation of cells.

Delivery of PAM or PAM encoding vector can be achieved by a variety of techniques known in the art. For example, for introduction into cells in vitro, electroporation, microinjection, cell fusion, DEAE dextran, calcium phosphate precipitation, gene gun, or DNA vector transporter can be used. The PAM or PAM encoding vector can also be introduced in vitro or in vivo by lipofection. Liposomes are commonly used for delivery of nucleic acids.

In one embodiment, the delivery of a PAM encoding vector is achieved by using an adenovirus. In various embodiments, polynucleotides encode a PAM in a viral expression vector. In general, suitable viral expression vectors comprise a modified viral genome having expression control sequences that are operatively linked to a PAM coding sequence to be expressed in cells into which the viral expression vector is introduced. Any viral expression vector can be used. In one embodiment, PAM may be delivered using modified adenoviral vectors. Adenoviral vectors that can be modified to express a PAM according to the present disclosure are commercially available, such as from Clontech. In general, the genome of a modified adenovirus for use with this disclosure will include a deletion in one or more of the adenoviral early gene regions, a site into which a PAM coding sequence is inserted, and expression control elements. The PAM coding sequence may be operatively linked to expression control elements in a manner which permits transcription, translation, and expression of the PAM in a cell. Conventional control elements are known in the art and include but are not necessarily limited transcription initiation, termination, promoter and enhancer sequences, RNA processing signals, and the like. If desired, the modified adenovirus can include a control element such as a tissue-specific promoter, such as an olfactory sensory neuron (OSN) or olfactory epithelium specific promoter. In one embodiment, the viral vector is a modified adenovirus with a CMV promoter. In embodiments, the adenovirus is an Ad5 adenoviral vector. Ad5 adenoviral vectors are known in the art and are commonly used for a variety gene delivery approaches and can be introduced into many different cell types. Ad5 vectors in general utilize Coxsackie-Adenovirus Receptor (CAR) to enter cells.

Given the benefit of the present disclosure, the skilled artisan will be able to construct adenoviral vectors and make compositions suitable for introducing a PAM into OSNs. In particular, those skilled in the art will realize that there are a variety of ways in which adenoviral preparations can be made and administered. Adenoviral particles may be used, which can be replication competent or replication defective. Techniques for producing adenoviral particles are well known in the art. The disclosure includes modifying the cellular tropism of the vectors by, for instance pseudotyping particles with envelope proteins or other surface antigens from other viruses, or by modifying the virus to include any other component that is desirable for targeted expression of the PAM in the OSNs. Where necessary the use of helper viruses may be made, such as adeno-associated virus, in order to make and/or use the modified adenoviruses for introduction of PAMs into OSNs, or to other cells. The modified adenoviral vectors can be formulated for administration via any acceptable route. Single or repeated administrations can be used to achieve adequate PAM expression in isolated OSNs or in OSNs in the nasal epithelium. In one embodiment, the adenoviral vector preparations are suitable for nasal administration.

In other approaches, genetically engineered mammals, such as transgenic mammals or those produced using conventional knock-in techniques can be used so that the mammal expresses a PAM in some or all of its OSNs. In embodiments, the genetically engineered mammals are rodents, such as mice.

Odorant solutions can be applied to cells in vitro by adding the solutions to the culture medium. If transient exposure is desired, the medium can be washed away after the desired exposure time. For delivery of odorant to the intact epithelium for in-vivo. preparation standard devices known in the art can be used. An example of such device is an odor puffer based on solenoid or manual valve activation. For delivery to the nasal epithelium, suitable compositions can be introduced using standard devices known in the art for intranasal delivery. For example, a whole animal is position in front of the odor delivery outlet which brings a stream of odorized air to the animal nose. The odor delivery can be initiated by manual or solenoid valve activation. The delivery of an odorant to the nasal cavity occurs via animal's inhalation of odorized air. There are several known devices for effecting intranasal delivery of compositions. Such devices include, for example, squeeze bottles, pressurized containers, pump-type containers, droppers, microfine powder dispersers, and nebulizers.

Once a PAM has been introduced in the OSNs, the OSNs are exposed to a test odorant. Simultaneously, or after a suitable period of time, the OSNs are exposed to the external stimulus that will modify a functional output of PAM such that the change is detectable. In one embodiment, light will be delivered to OSNs for activation of the photoconversion of PAM which comprises a color shift of fluorescence emitted by the PAM from green to red, or an increase in brightness of the fluorescence, or an increase in a red-to-green ratio of the fluorescence, or a combination thereof. In an embodiment, the light to which the OSNs/PAM is exposed has a wavelength of 340-420 nm, inclusive, and including all digits and ranges of digits therebetween.

For in-vitro preparation, such as cultured OSNs or intact epithelium, the light can be shined directly to OSNs. For in-vivo assay, the light can be delivered either to the nasal cavity via optical fiber or shined to the OSNs' axonal terminals in the OB. In the whole animal assay the delivery of the light to OSNs will be synchronized to odorant delivery, which is controlled by airflow to the nose. The light will be delivered after the onset of inhalation natural or artificial followed by an onset of odor delivery to the space in front of the nose. In case when a single odor and light exposure is insufficient for detectable PAM activation, multiple odor exposures synchronized with light exposure can be used.

In another embodiment for PAM activated by other means like electromagnetic field or chemical application, the delivery of the correspondent stimulus (E-M field or chemical) is synchronized with odor delivery and OSNs activation.

After exposure of the OSNs to the odorant and the external stimulus for PAM, the OSNs can be collected. If the exposure was done for OSNs in vivo, olfactory epithelia with the underlining stroma can be obtained. In the case of animals, the olfactory epithelia can be harvested from the nasal cavity by dissecting away the surrounding cartilage tissue. For obtaining samples from human subjects, tissue biopsies can be obtained and processed. The human OSNs can be harvested, PAM can be expressed in human OSNs and the in-vitro assays can be used to identify human OR sensitive to a specific odorant After enzymatic treatment, stroma is removed from the olfactory epithelia by microdissection. The cells can be enzymatically dissociated. For example, in one embodiment, the cells can be dissected out in a physiological buffer solution (such as Ringer's solution) and then used for isolation of OSNs that have reacted to the odorant.

OSNs that express the OR which reacts to the odorant will have a detectable signal from the PAM. Individual OSNs that produce the detectable signal can be separated from one another and from OSNs that do not express detectable signal. Genes encoding the OR in each separated OSN can be sequenced using conventional methods. The signal from the PAM may be a signal comprising emission of fluorescent spectra upon excitation using light of a particular wavelength. OSNs that produce such signals can be separated from one another using cell sorting techniques, including but not limited to, fluorescence activated cell sorting (FACS) Once individual OSNs are separated the OR-encoding genes can be sequenced using, for example, PCR-based amplification and sequencing techniques. PCR primers can be designed to sequence OR genes for each separated OSN based on common OR gene sequences, or common sequences which flank OR sequences, or using redundant primer-based approaches. Alternatively, all OSNs that produce detectable signals can be pooled and individual OR-encoding genes can be determined using any of a variety of commercially available next-generation sequencing techniques which facilitate nucleotide sequence determination of complex mixtures of polynucleotides. OR sequences can be determined based on analysis of genomic DNA sequence, or mRNA sequences. Once the nucleotide sequences of the ORs are determined, the primary amino acid sequence and therefore the identity of the particular OR responsive to the particular test odorant can be deduced.

In one aspect of the invention, the sequence of activation of different OSNs in response to an odorant can be determined. The sequence of activation OSNs is considered to be important for odor perception. While not intending to be bound by any particular theory, it is considered that in an intact epithelium the most sensitive receptors will be excited first, thus bringing the problem of finding the most sensitive receptor into temporal domain, i.e. to identify the receptor that is excited first. Therefore, in one embodiment, the present method can be used in conjunction with multiple brief but temporally precise external stimulation synchronized with odor delivery.

In one embodiment, using the photo-switchable PAMs during an episode of odor exposure to a whole animal or isolated epithelium, brief pulses of light can be synchronized with odor delivery, thus registering of only the very first OSN (and thus most sensitive) activated by a given odorant. The very short light exposure period can be compensated by multiple stimulus presentations. Each exposure accumulates permanent marker, but only in the neurons active at this specific temporal interval. This method, allows for the identification of correspondent OR genes from OSN active in various temporal windows, potentially isolating the most sensitive ORs that respond to a particular odorant. This method using short pulses of light is termed herein as the stroboscopic method.

In general, this "stroboscopic" method, i.e., synchronization of brief light exposure to repeatable processes, can be used for other neuronal identification in other well-controlled conditions, such as sensory or motor tasks.

In one embodiment, the pulses of light are synchronized with internal rhythm, such as breathing/sniffing etc. For example, a pulse may be presented at the specific phase of the sniff cycle and the duration of the pulse can be from 0.01 ms to the duration of the rhythm period (such as duration of the sniff). In general the average duration of a sniff is about 300 ms. In one embodiment, duration of a sniff may be from 50 ms to 1 second. In one embodiment, it may be shorter than 50 ms or may be longer than 1 second. In one embodiment, the number of pulses may be from 1 to 10, or 1 to 100 and all integers and ranges therebetween.

In one aspect, this disclosure provides an isolated population of OSNs. In one embodiment, this disclosure provides isolated OSNs where all or a majority of the OSNs are activated by the same odorant. In various embodiments, the population may contain 50, 60, 70, 80, 90, 95 and 99% and all percentages between 50 to 100, OSNs that respond to the same odorant. In another embodiment, from 50 to 100% (and all integers therebetween) of the OSNs in the isolated population of OSNs express the same OR gene. In another embodiment, from 50 to 100% (and all integers therebetween) of the OSNs in the isolated population of OSNs display the same sensitivity to a given odorant. By same sensitivity is meant that the OSNs are activated at about the same time Delivery of the odorant to intact animal and delivery of the light at each odor presentation accumulates some amount of permanent marker in OSNs, The marker (for example, photo converted protein) will diffuse along the axons and will be detectable in the axon terminals in OB glomeruli. Thus, in one embodiment, an assay to identify the positions of glomerulus for OR receptors activated by a given odorant may be used.

In one embodiment, the fluorescence from an OSN is normalized for the amount of light delivered to it. For determination of the amount of light delivered, an indicator, which is sensitive to light at wavelengths that photoconvert CaMPARI, but which is not sensitive to calcium, may be used. If such an indicator (termed herein as dose indicator) has an emission wavelength that overlaps with the fluorescence emission of the PAM, then the dose indicator may be distinguished from the PAM by spatial distribution. For example, a dose indicator may be used that is selectively or exclusively expressed in the nucleus. Thus, even if its fluorescence overlaps with that of PAM, because of their differential distribution within the cell (cytoplasm versus nucleus), the amount of fluorescence from the dose indicator can be distinguished from, and used to normalize the PAM fluorescence in different OSNs. An example of a dose indicator that is sensitive to light irrespective of intracellular calcium concentration is mEos2. Using established methods to clone a nuclear localization signal to this protein would restrict its localization to the nucleus. The mEos2 excitation, emission and, importantly, photoconversion spectra are nearly identical to CaMPARI v1, but the spatial localization (nuclear vs cytoplasmic, respectively) will allow separation of mEos2 and CaMPARI signals using established microscopy techniques while ensuring that these two protein species receive approximately equal doses of light during photo conversion.

Figure 7:
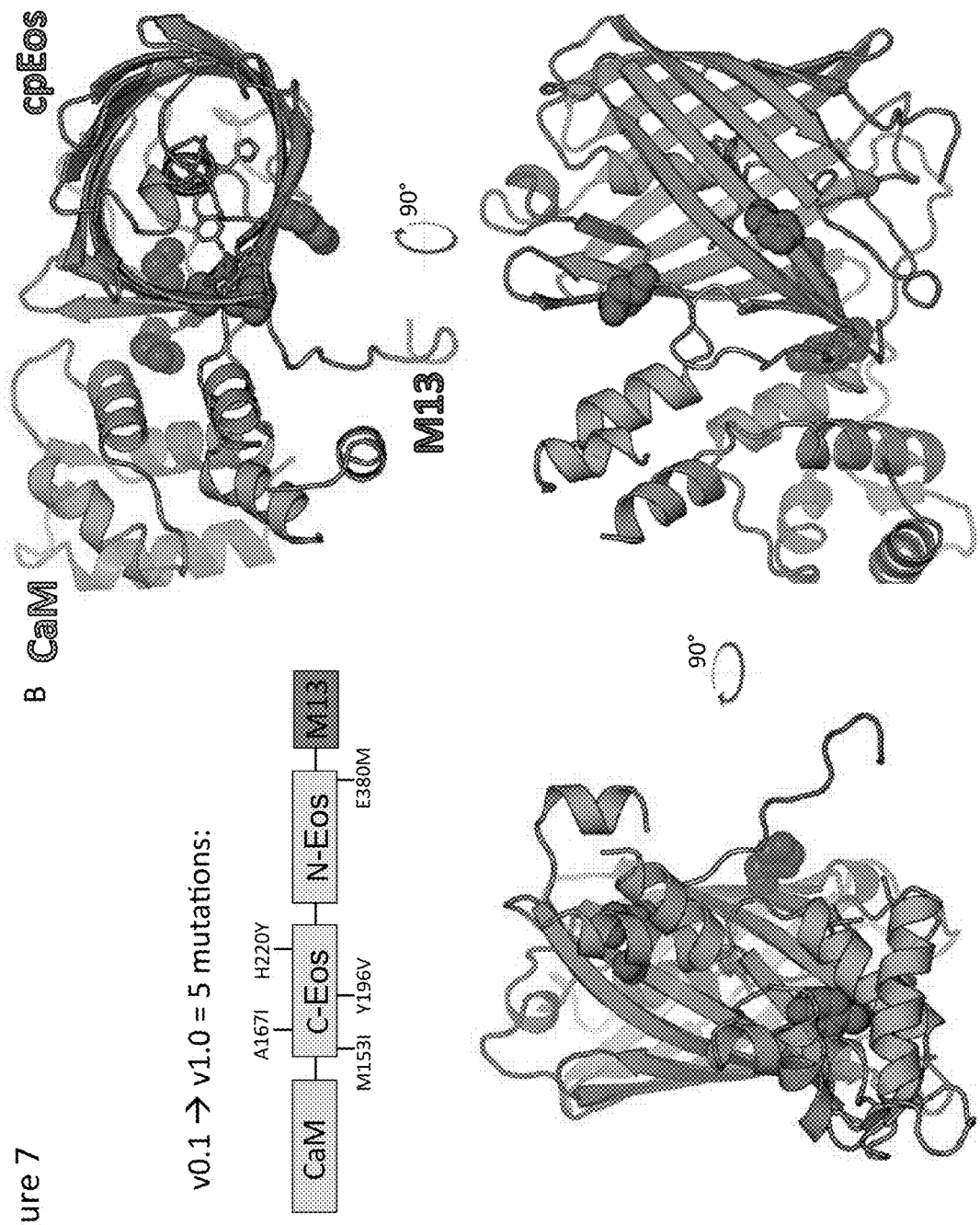
FIG. 7 includes (A) a diagram showing the five amino acid mutations to CaMPARI v0.1 that produce CaMPARIv1.0 and (B) illustrations of CaMPARI v1.0 showing the location of the amino acid mutations.

The sequences provides in this disclosure are as follows:

SEQ ID NO: 1 is an amino acid sequence of an embodiment of an isolated polypeptide comprising CaM, EosFP, and M13 (i.e., CaMPARI v1). The sequence of CaMPARI v0.1 (FIG. 4) differs from CaMPARI v1.0 as shown in FIG. 7.

SEQ ID NO: 2 is an amino acid sequence of the mEos C-terminus portion of CaMPARI v1.

SEQ ID NO: 3 is an amino acid sequence of the mEos N-terminus portion of CaMPARI v1.

SEQ ID NO: 4 is an amino acid sequence of the CaM portion of CaMPARIv1.

SEQ ID NO: 5 is an amino acid sequence of the M13 portion of CaMPARI v1.

SEQ ID NO: 6 is an amino acid sequence of the NES portion of CaMPARI v1.

SEQ ID NO: 7 is a nucleotide sequence encoding the isolated polypeptide of SEQ ID NO: 1.

SEQ ID NO: 8 is an amino acid sequence of another embodiment of an isolated polypeptide comprising CaM, EosFP, and M13.

SEQ ID NO: 9 is a nucleotide sequence encoding the isolated polypeptide of SEQ ID NO: 8.

SEQ ID NO: 10 is an amino acid sequence of another embodiment of an isolated polypeptide comprising CaM, EosFP, and M13, the EosFP including a circular permutation within beta strand number 8.

SEQ ID NO: 11 is a nucleotide sequence encoding the isolated polypeptide of SEQ ID NO: 10.

SEQ ID NO:12 is a sequence for nuclear export sequence.

SEQ ID NO:13 is the sequence for mEos2 protein (Nat Methods. February 2009; 6(2): 131-133).

The details of one or more embodiments of the presently-disclosed subject matter are set forth in this document according to all of the foregoing description and the following description. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom.

The presently-disclosed subject matter includes a method for using the disclosed isolated polypeptides to detect particular ions or small molecule analytes in OSNs. The presently-disclosed subject matter also includes a method for using complementary DNA (cDNA) sequences encoding the isolated polypeptides for detection of changes in OSNs.

The term "isolated", when used in the context of an isolated nucleotide or an isolated polypeptide, is a nucleotide or polypeptide that, by the hand of man, exists apart from its native environment and is therefore not a product of nature. An isolated nucleotide or polypeptide can exist in a purified form or can exist in a non-native environment such as, for example, in a transgenic host cell.

Additionally, the terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

In some embodiments the isolated polypeptides useful for the method of the present disclosure comprise a fluorescent polypeptide, a compound-binding polypeptide, and a polypeptide target of the compound-binding polypeptide (polypeptide target), as well as variants and/or fragments of any of the polypeptides. The individual polypeptides that comprise the isolated polypeptide can be arranged in any fashion. For instance, some embodiments of isolated polypeptide can comprise, from the N-terminus to C-terminus, the compound-binding polypeptide, the fluorescent polypeptide, and the polypeptide target. In other embodiments the isolated polypeptide can comprise, from the C-terminus to N-terminus, the compound-binding polypeptide, the fluorescent polypeptide, and the polypeptide target.

The fluorescent polypeptides (FP) as discussed herein generally refer to polypeptides comprising a chromophore. After synthesis and folding of the isolated polypeptide, the chromophore can emit a florescence. The chromophore can be an amino acid segment, including the amino acid segment HYG. Fluorescent polypeptides can experience a particular photoconvertible color shift when the isolated polypeptides contact a detecting substance, such as a particular ion or small molecule analyte.

Therefore, in some embodiments of the isolated polypeptides the fluorescent polypeptides can include photoconvertible fluorescent proteins. There is no particular limitation on the color shift that the photoconvertible fluorescent proteins can exhibit. Exemplary photoconvertible fluorescent proteins include, but are not limited to, PS-CFP (cyan-to-green photoconversion) and PSmOrange (orange-to-far red photoconversion) polypeptides. The fluorescent polypeptides also include green-to-red polypeptides including, but not limited to, Kaede, KikGR, mClavGR2, mMaple, Dendra, IrisFP, and NijiFP. See also, for example, the fluorescent polypeptides described in U.S. Patent Application Publication No. 2011/0214192 to Wang et al.

In some embodiments the fluorescent polypeptides are selected form dim-to-bright photoactivatable fluorescent polypeptides. Exemplary dim-to-bright photoactivatable fluorescent polypeptides include, but are not limited to, PA-GFP and PAmCherry. Similar to color shifting fluorescent polypeptides, the extent to which dim-to-bright polypeptides undergo photoactivation can depend on the concentration of a detecting substance (e.g., ion or analyte).

As stated above, in some embodiments the polypeptides are variant and/or fragment polypeptides. The term "variant" refers to an amino acid sequence that is different from the reference polypeptide sequence by the location or type of one or more amino acids. Thus, a variant may include one or more amino acid substitutions. The terms "polypeptide fragment" or "fragment", when used in reference to a reference polypeptide, refer to a polypeptide in which amino acid residues are deleted as compared to the reference polypeptide itself, but where the remaining amino acid sequence is usually identical to the corresponding positions in the reference polypeptide. As mentioned above, such deletions can occur at the amino-terminus, carboxy-terminus of the reference polypeptide, or alternatively both. A fragment can also be a "functional fragment," in which case the fragment retains some or all of the activity of the reference polypeptide as described herein.

In this regard, in some embodiments the fluorescent polypeptide can be circularly permutated and/or comprise amino acid substitutions. In one embodiment the fluorescent polypeptide is a an Eos fluorescent polypeptide (FP), and preferably is a circularly permutated mEos2 polypeptide that includes the mutations V2ins, F34Y, S39T, A69V, L93M, and I102Y (referred to herein as CaMPARI v1 isolated polypeptide). The amino acid sequence of the exemplary fluorescent polypeptide of CaMPARI v1 is shown in SEQ ID NOS: 2 and 3, which are the C-terminus and N-terminus portions of the fluorescent polypeptide, respectively.

The fluorescent proteins can have circular permutations on beta strands of the polypeptides. In the case of EosFP, it can be beneficial to include circular permutations on beta strands 1, 5, 7, 8, and/or 9. For example, SEQ ID NO: 10 shows an amino acid sequence of an isolated polypeptide having a circular permutation on beta strand 8 of the EosFP. Those of ordinary skill in the art, upon reviewing the entire disclosure of this paper, will appreciate similar circular permutations or mutations that can be performed on other fluorescent proteins to enhance their ability to detect a substance.

With regard to the compound-binding polypeptides, these polypeptides can be selected from polypeptides that can selectively bind particular substances. The compound-binding polypeptides therefore permit the isolated polypeptide to bind to one or more particular substance. Isolated polypeptides with compound-binding polypeptides can therefore act as an integrator, and possibly also as a negative indicator, for the particular substance that the compound-binding polypeptide can bind to. Exemplary detecting substances that can be bound by compound-binding polypeptides include ions and small molecule analytes. Detecting substances can include substances that have significant roles in cellular pathways.

In certain embodiments the compound-binding polypeptide is calmodulin (CaM) polypeptide, or variants and/or fragments thereof (e.g., SEQ ID NO: 4). CaM binds to calcium, and permits the isolated polypeptide to act as an integrator for calcium. In turn, calcium detection can be used to trace neurons, measure neuronal activity, or the like.

As stated above, the isolated polypeptide also comprises a polypeptide target of the compound-binding polypeptide. The polypeptide target can interact selectively with a compound-binding polypeptide that is bound to a detecting substance. For instance, in an exemplary isolated polypeptide that comprises the compound-binding polypeptide CaM, the polypeptide target can be a M13 polypeptide, or a variant and/or fragment thereof (e.g., SEQ ID NO: 5). M13 can selectively interact with the calcium-bound form of CaM. Some embodiments also comprise variants and/or fragments of any polypeptide target. For example, some embodiments of isolated polypeptides comprise the polypeptide target M13 having one or more amino acid mutations selected from the group consisting of S2L, W6Y, W6L, W6V, W6M, W6H, W6F, T9A, T9D, G10D, G10A, H11K, V13H, V13S, V13T, V13A, V13D, and V13L.

Accordingly, in specific embodiments the isolated polypeptide comprises an EosFP polypeptide, a CaM polypeptide, and a M13 polypeptide, or variants and/or fragments thereof. The EosFP polypeptide can include a C-terminus portion and an N-terminus portion. Exemplary C-terminus and N-terminus portions of a EosFP polypeptide can comprise the amino acid sequence of, respectively, SEQ ID NO: 2 and SEQ ID NO: 3. Furthermore, the N-terminus portion and the C-terminus portion of any fluorescent polypeptide can be joined together via an inter-domain linker that is disposed therebetween. Exemplary linkers can comprise about 4 to about 20 amino acids. In some embodiments the inter-domain linker is six amino acids in length. In certain embodiments the inter-domain linker comprises the amino acid sequence GGTGGS. (SEQ ID NO: 16).

Additionally, since the polypeptides that comprise the isolated polypeptide may be ordered in different sequences, the polypeptide can comprise the CaM polypeptide, the EosFP polypeptide, and the M13 polypeptide from an N-terminus to a C-terminus of the isolated polypeptide. On the other hand, another exemplary polypeptide can comprise, from a C-terminus to an N-terminus, the CaM polypeptide, the EosFP polypeptide, and the M13 polypeptide. For instance, SEQ ID NOS: 1 and 8 show the amino acid sequences of exemplary isolated proteins that, among other things, have opposing orientations of the CaM polypeptide, the EosFP polypeptide, and the M13 polypeptide.

In some embodiments the isolated polypeptide further comprises a first polypeptide linker disposed between the compound-binding polypeptide and the fluorescent polypeptide. Some embodiments also comprise a second linker polypeptide disposed the fluorescent polypeptide and the polypeptide target. The linker polypeptides can be for purification of the isolated polypeptide. For instance, in some embodiments at least one of the linker polypeptides is a hexahistidine tag (6x His tag) that can be used to purify the protein using affinity chromatography. In some embodiments at least one linker can be a restriction site used in the assembly of DNA, such as XhoI or MluI. Those of ordinary skill will appreciate other linker polypeptides that can be incorporated into the isolated polypeptides for purification purposes, as restriction sites, or the like.

The isolated polypeptides useful for the method of the present disclosure can also comprise a nuclear export signal (NES). The NES can signal for export of the isolated protein from the cell nucleus. Thus, isolated polypeptides that comprise an NES can allow the isolated polypeptide to be expressed in the nucleus and the cytoplasm of eukaryotic cells. Consequently, the addition of a NES can, among other things, allow the isolated polypeptide to detect substances outside the cell nucleus. The NES may be located at the N-terminus or the C-terminus of the isolated polypeptide. One exemplary NES is one that comprises an amino acid sequence of SEQ ID NO: 6.

In some embodiments, nucleic acid molecules (e.g., cDNA) that encode an isolated polypeptide may also be used for the method of the present disclosure. In some embodiments the nucleic acid molecule comprises a nucleic acid molecule encoding a polypeptide that comprises CaM, EosFP, and M13, or mutations and/or fragments thereof. Exemplary nucleic acid sequences include those represented by SEQ ID NOS: 7, 9, and 10. In certain embodiments the nucleic acid molecule that encodes the isolated peptide is cDNA.

The terms "nucleotide," "polynucleotide," "nucleic acid," "nucleic acid sequence," and the like refer to deoxyribonucleotides or ribonucleotides and polymers thereof in either single or double stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified versions thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed base and/or deoxyinosine residues (Batzer et al. (1991) Nucleic Acid Res 19:5081; Ohtsuka et al. (1985) J Biol Chem 260:2605 2608; Rossolini et al. (1994) Mol Cell Probes 8:91 98). The terms are inclusive of cDNA molecules.

In some embodiments the nucleic acid molecule is a molecule that encodes a portions of an isolated polypeptide, including any of the portions described herein. For instance, the nucleic acid molecule may encode for a compound-binding polypeptide (e.g., CaM), a fluorescent polypeptide (e.g., EosFP), and/or a polypeptide target (e.g., M13). Other embodiments of nucleic acid molecules can encode for the first polypeptide linker, the second polypeptide linker, the inter-domain linker, the NES, or any combination thereof of any of the isolated polypeptides described herein.

Further still, the presently-disclosed subject matter includes a method of detecting an ion or small molecule analyte (detecting substance) in a sample of cells comprising OSNs. In some embodiments the method comprises providing a sample that includes cells, contacting the sample with an embodiment of the present isolated polypeptides, exposing the sample that has contacted the isolated polypeptide to light, and then detecting the presence of the detecting substance. The term "sample" refers to a sample from the subject, said sample comprising a cell, for example, blood, plasma, organ tissue, or any other sample that may comprise an OSN from the subject.

In some embodiments, the sample includes neurons from the OB. In some embodiments the sample may include cells other than OSNs. The detecting substance can be calcium, which plays a role in neuronal signaling. Thus, the present methods can utilize the isolated polypeptides to label "active" cells during a particular stimulus, and quantify and characterize calcium activity in response to that stimulus. Similarly, the present methods can be used to trace neurons based on their calcium activity. Those of ordinary skill will appreciate further uses for detecting methods that utilize the present isolated polypeptides.

There are various ways that the isolated polypeptide can be made to contact a sample. In some embodiments the isolated polypeptide is injected directly or via a carrier to a particular site that includes the cells that are to be observed. In other embodiments the isolated polypeptide is transgenically delivered to cells that comprise a sample. The term "transgenic" and the like is used herein to refer to introducing particular genetic material into the genome of a cell or organism. Thus, cells that have had the gene for the isolated polypeptide for the isolated polypeptide transgenically delivered to the cells can express the isolated polypeptide themselves.

With regard to the exposing step, a sample may be exposed to any type of light and for any duration that induces a change in fluorescence of the isolated polypeptide. In color-changing photoconvertible polypeptides, exposure to light will induce a color shift in the polypeptides that can be dependent on the concentration of a detecting substance in the sample. The duration of time that a sample is exposed is not particularly limited. In some embodiments sample is exposed for a time period sufficient to expose the cells within a particular volume of sample. In specific embodiments the light for exposing a sample can be emitted for a time period of about 0.01 millisecond, 0.05 millisecond, 0.1 millisecond, 0.5 millisecond, 1 millisecond, 10 milliseconds, 100 milliseconds, 500 milliseconds, 1 second, 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, or 10 minutes, and all values between 0.01 milliseconds and 10 minutes to the $100^{th}$ of a second, and all ranges therebetween. In one embodiment, the light exposure may be higher than 10 minutes or lower than 0.01 milliseconds.

The type of light that is used to expose a sample is generally only limited in that it should comprise a wavelength that can stimulate a particular photoconversion, photoactivation, or the like. The term "light" refers to any electromagnetic radiation including, but not limited to, visible light, microwave light, ultraviolet light, or the like. The light can have a wavelength of about 100 nm, about 200 nm, about 300 nm, about 400 nm, about 500 nm, about 600 nm, about 700 nm, about 800 nm, about 900 nm, or about 1000 nm. The light may also have a wavelength falling either above or below these recited wavelengths so long as it can induce a photoconversion or photoactivation in the isolated polypeptide. In one embodiment, the range is from about 350 to 430 nm. In one embodiment, it is from 340 to 420 nm.

Once the sample with the isolated polypeptide has been exposed to light, one can detect the presence of a detecting substance in the sample. The presence of a detecting substance can be evidenced by a color shift of the fluorescence emitted by the isolated polypeptide. The presence of a detecting substance can also be evidenced by a change in the intensity of a fluorescence emitted by an isolated polypeptide. Thus, the presence and/or degree of a change in fluorescence of an isolated polypeptide can be indicative of the presence and/or concentration of a detecting substance in a sample.

In this regard, in some embodiments the presence of a detecting substance can be measured by observing the extent of the color shift in an isolated polypeptide. In some embodiments the greater the extent of the color shift the higher the concentration of the detecting substance in the sample. For instance, with a green-to-red isolated polypeptide that can detect calcium, the isolated polypeptide will display a higher percentage and/or amount of red fluorescence as the concentration of calcium increases. Furthermore, in some embodiments of the present methods that utilize isolated polypeptides that shift from a first color to a second color, the presence of a detecting substance can be measured by observing a change in a ratio of the second color to the first color. In other words, the higher the ratio of the second color to the first color, the higher the relative concentration of the detecting substance. Utilizing a ratio to detect the presence of detecting substance can be advantageous since the method is mostly if not entirely independent of expression level rather than the total concentration of a detecting substance.

In some embodiments the fluorescence color or intensity change experienced by an isolated polypeptide that has contacted a detecting substance and has been exposed to light can be permanent or nearly-permanent. The term nearly-permanent refers to a change that lasts for a time period sufficient to allow for analysis of a sample outside of just one field of view (e.g., of a standard microscope performing live imagine), thereby permitting a user to scan an area that is greater than a field of view to quantify and characterize the presence of a detecting substance. This permits the measure of activity over relatively larger areas of tissue, does not require real-time imaging, and permits measurement to be conducted after preparing tissues by, for example, fixing or sectioning tissues.

In some embodiments the isolated polypeptides thus function as an integrator of a detecting substance. The integrators detect the presence of, and particular concentration increases, a detecting substance in a sample. In this regard, the term "integrator" as used herein refers to compounds having signals that permanently or substantially permanently increase over time, as they are exposed to light, at a rate that is dependent on the contraction of a detecting substance. Integrators can exhibit an increasing signal over time even though the concentration of a detecting substance may fluctuate up and down.

Exemplary isolated polypeptides can also function as an indicator. In some embodiments the isolated polypeptides are negative indicators of a detecting substance that can indicate whether a substance lacks a particular detecting substance. In this regard, the term "indicator" as used herein refers to compounds that exhibit a signal that is dependent on the concentration of a detecting substance, wherein the signal fluctuates in accordance with fluctuations in concentration of the detecting substance.

In some embodiments the isolated polypeptides function as both integrators and as negative indicators of a detecting substance.

Accordingly, the presently-disclosed subject matter includes methods of using the isolated polypeptides as described herein as a reporter for ion activity, as a sensor for an analyte, as an agent for imaging experiments, and the like. The presently-disclosed subject matter further includes a method of producing an isolated polypeptide or nucleic acid molecule as described herein, using the methods and schemes as set forth in the Examples and Figures, for example.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is illustrated by the following specific but non-limiting examples. The following examples may include compilations of data that are representative of data gathered at various times during the course of development and experimentation related to the present invention.

EXAMPLE 1

This Example describes procedures used to design and synthesize novel fluorescent proteins. This Example further describes procedures used to optimize and characterize the novel fluorescent proteins.

Circular permutation of fluorescent protein domains and attachment to ligand binding domains can allow modulation of fluorescence intensity through conformational rearrangement of the FP chromophore chemical environment driven by ligand binding. Thus, the procedures utilized a circular permutation of a photoconvertible fluorescent protein to attempt to permit modulation of photoconversion efficiency of the protein in a ligand-dependent manner (FIG. 1).

To construct a fluorescent protein that would undergo more efficient green-to-red photoconversion in the presence of calcium, libraries were created and screened for circularly permuted EosFP variants fused at the termini to calmodulin (CaM) and the calmodulin-interacting peptide M13. Circularly permuted variants of mEos2 (SEQ ID NO:13) were generated carrying the additional mutations V2ins, F34Y, S39T, A69V, L93M, I102Y by PCR amplification from a template comprising tandem copies of the variant Eos gene separated by a linker encoding GGTGGS (SEQ ID NO: 16). The first copy of the variant Eos gene lacked a stop codon. The PCR reaction included five forward primers and five reverse primers to allow variation in the position/length of each terminus, yielding 25 distinct combinations of termini. Each primer additionally contained one NNS variable codon to allow variation in amino acid sidechain at each FP terminus. PCR products were ligated between M13-CaM or CaM-M13, yielding a total theoretical library size of 20,000. Eleven such libraries were created, centered on the middle of each of the eleven beta strands of Eos.

Figure 2:
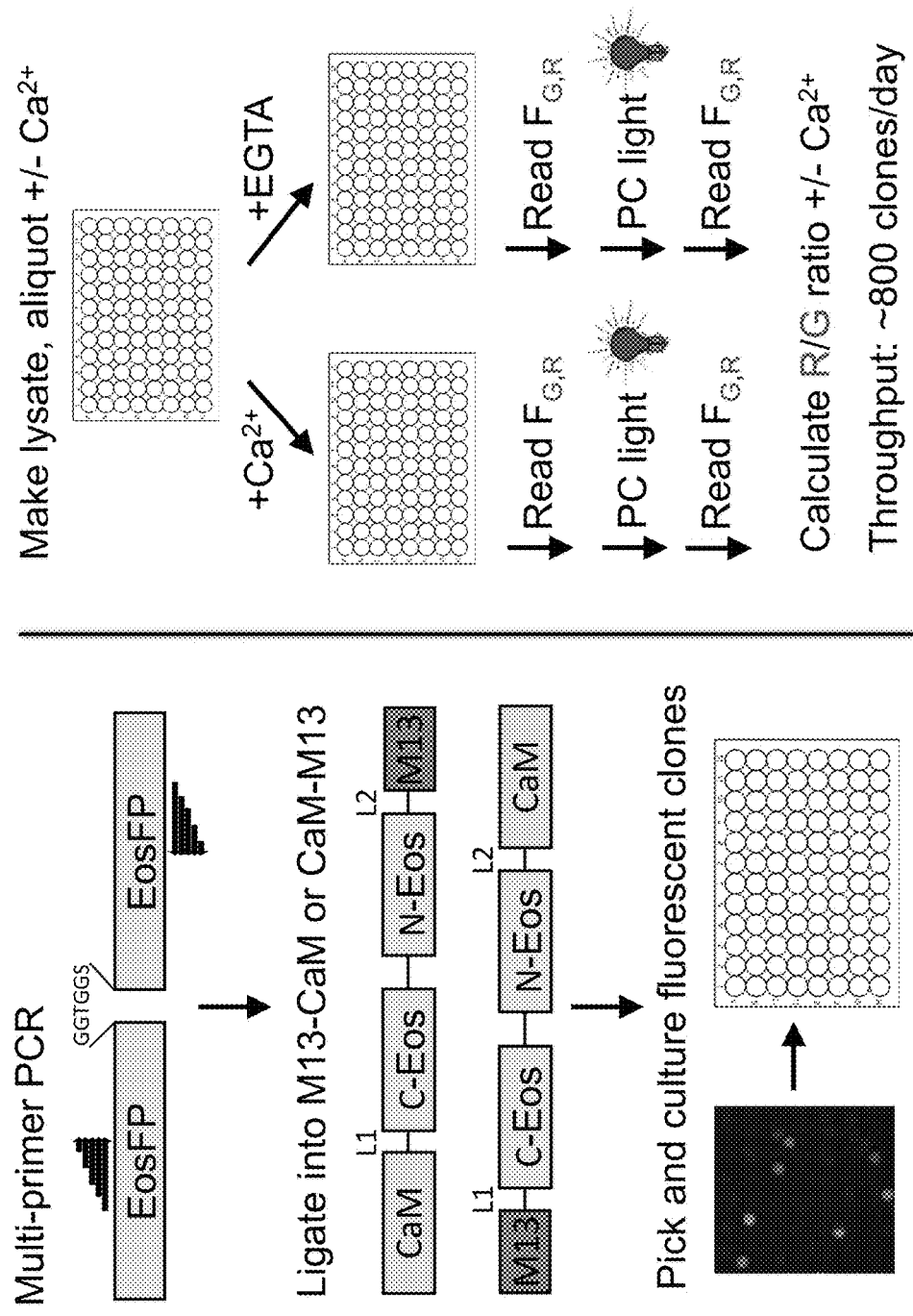
FIG. 2 includes a schematic showing an E. coli lysate screen protocol for embodiments of calcium-dependent photoconvertible proteins.

To screen for calcium-modulated photoconversion, libraries were transformed into T7 Express *E. coli* (NEB) and colonies that were visibly green fluorescent under a stereomicroscope after 48 h at 4° C. were picked into 1 mL of autoinduction media in 96-well blocks (FIG. 2). Cultures were grown at 30° C. for 36 h, harvested by centrifugation, and the cell pellets frozen at −20° C. Cell pellets were thawed and resuspended in 500 uL and shaken at 30° C. for 1 h to allow cell lysis. Cell debris was pelleted by centrifugation at 6100×g and 95 μL of each lysate was transferred to two separate 96-well microplates and mixed with calcium chloride and EGTA, respectively, to final concentrations of 0.5 uM and 1 uM. Green and red fluorescence was measured in a plate reader, followed by illumination with a 400 nm LED array (~200 mW/cm$^2$) for 80 s and another measurement of green and red fluorescence. Finally, the +/−calcium plates were switched by adding EGTA to 10 mM in the original calcium plate, and adding CaCl$_2$ to 5 mM in the original EGTA plate, and the green and red fluorescence was measured again.

For each library variant, the fluorescence change+/−calcium in both the green and red channels as well as the difference in the extent of photoconversion+/−calcium were calculated using the following formula:

$$\frac{\Delta R}{R_0} = \frac{\frac{F_R^{Ca^{2+}}}{F_G^{Ca^{2+}}} - \frac{F_R^{EGTA}}{F_G^{EGTA}}}{\mathrm{Min}\left(\frac{F_R^{Ca^{2+}}}{F_G^{Ca^{2+}}}, \frac{F_R^{EGTA}}{F_G^{EGTA}}\right)}$$

Figure 3:
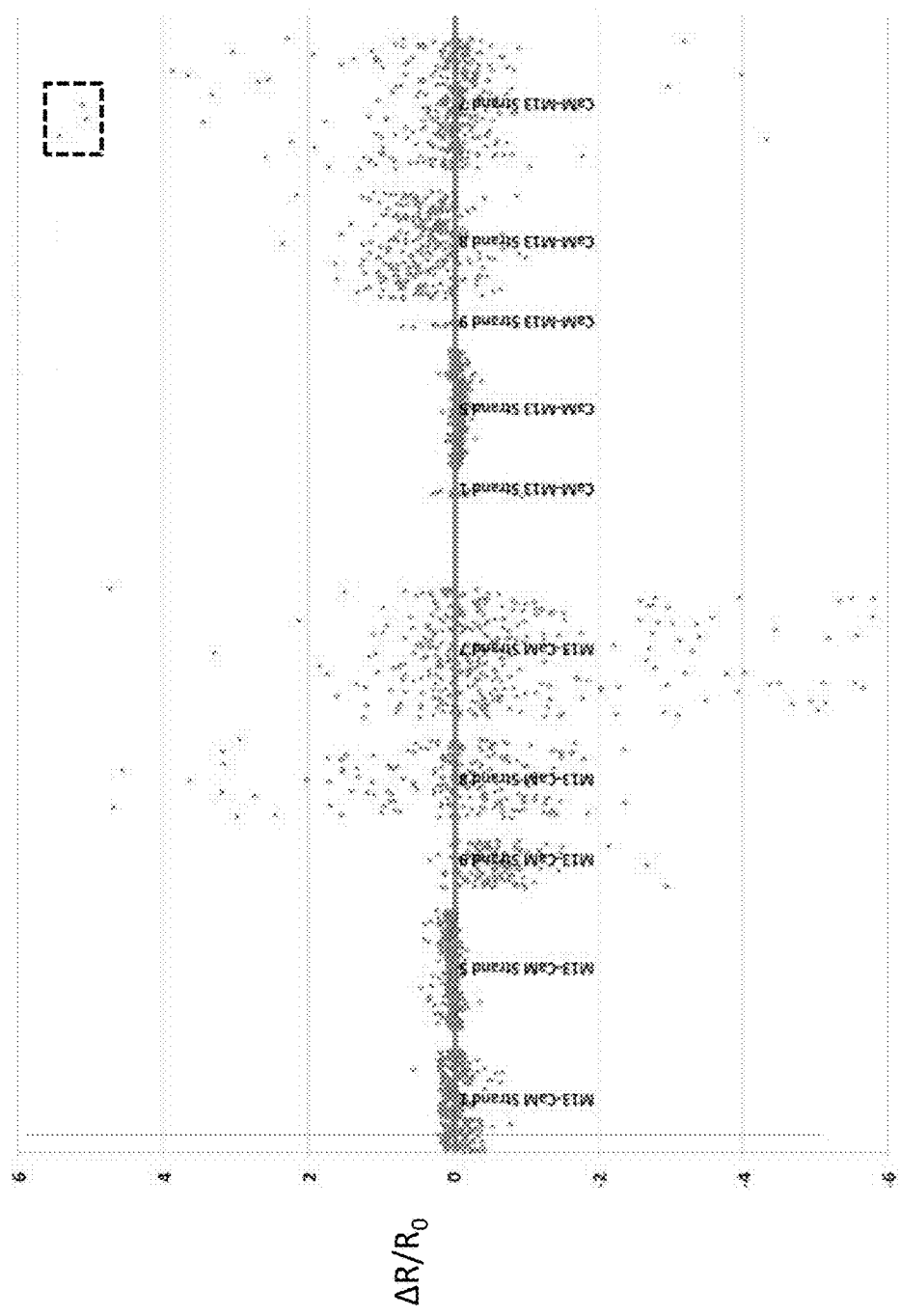
FIG. 3 includes a chart showing $\Delta R/R_0$ values for embodiments of calcium-dependent photoconvertible proteins analyzed using an E. coli lysate screening protocol, where each red dot represents one protein and dots are organized into groups by the beta strand of circular permutation library and the topology of the calcium sensing domains (CaMPARI v0.1 shown inside dashed box).

Up to 1600 fluorescent clones were screened per library. Only libraries within beta strands 1, 5, 7, 8, 9 exhibited a significant number of fluorescent colonies, and libraries within other beta strands of EosFP were non-fluorescent and not pursued. Individual library clones exhibited up to 5-fold more photoconversion in the presence of calcium (strand 7 library, CaM-M13 topology), or nearly 6-fold more photoconversion in the absence of calcium (strand 7 library, M13-CaM topology) (FIG. 3). The top three clones that photoconverted faster in the presence of calcium had identical sequences, and are shown in the dashed box in FIG. 3.

Figure 4:
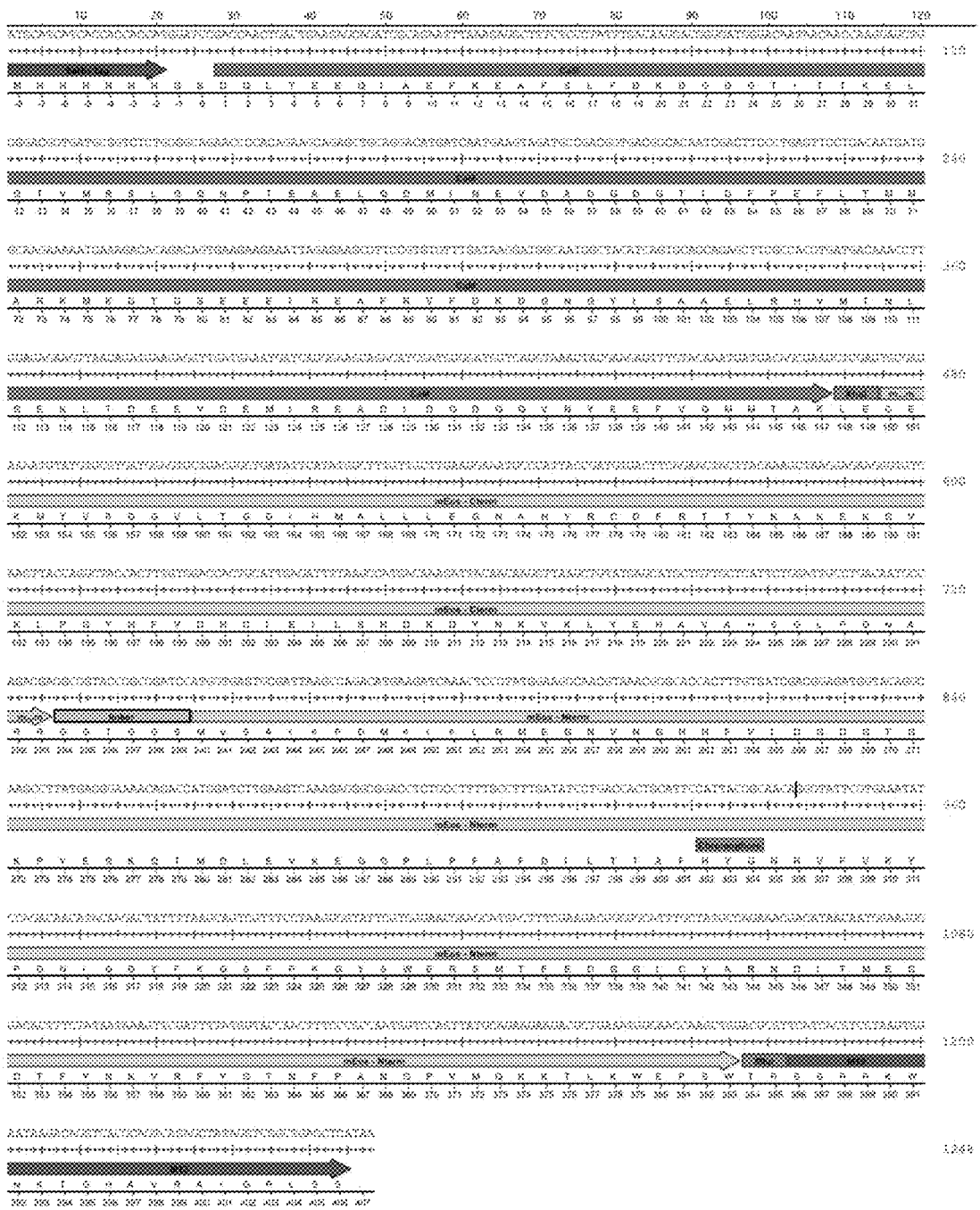
FIG. 4 includes a diagram showing the nucleotide and amino acid sequence of CaMPARI v0.1. The amino acid sequence is SEQ ID NO:14. v0 has 20 fewer amino acid residues and 6 mutational changes. The mutations from v0.1 to v1.0 are M-8S, M153I, A167I, Y196V, H220Y and E380M. The nucleotide sequence is SEQ ID NO:15.

These sequences were referred to as Calcium-Modulated Photoactivatable Ratiometric Integrator, version 0.1 (CaMPARI v0.1) (FIGS. 3 and 4).

For interesting library clones, a small amount of protein was expressed and purified to measure fluorescence brightness and calcium affinity. The variant exhibiting the best photoconversion contrast+/−calcium that maintained a reasonable fluorescence brightness and calcium affinity was selected for optimization. Optimization was carried out by saturation mutagenesis using NNS codons at individual codon positions within the FP domain and screening of each small library using the E. coli lysate assay described above. In a second round of optimization, combinations of beneficial single amino acid variants were generated in a small library and screened for photoconversion contrast+/−calcium.

Figure 6:
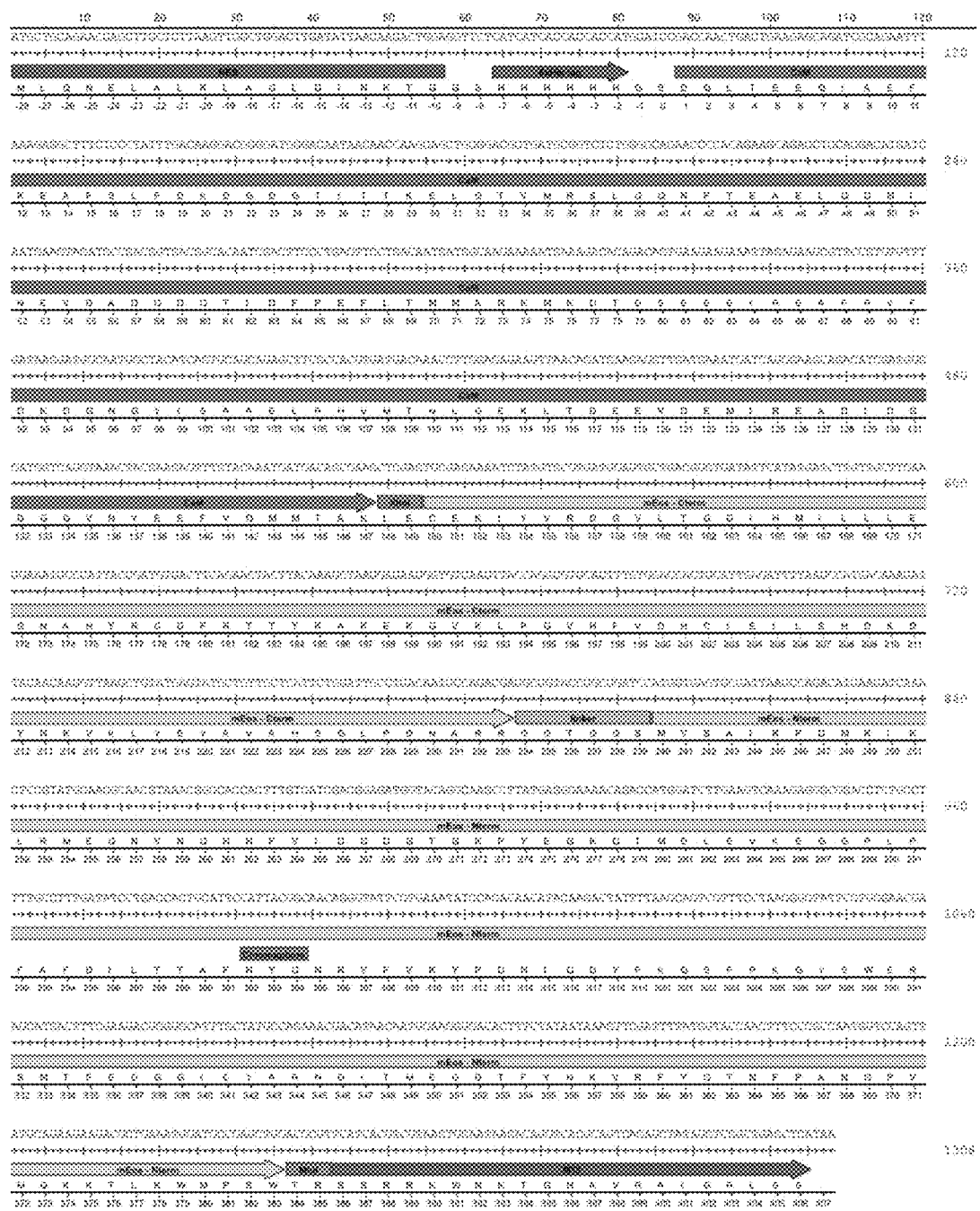
FIG. 6 includes a diagram showing the nucleotide and amino acid sequence of CaMPARI v1.0. The nucleotide sequence is SEQ ID NO: 7 and the amino acid sequence is SEQ ID NO: 1. There are 5 amino acid changes between CaMPARI v0.1 and v1.0. While CaMPARI v0.1 has M at 153, A at 167, Y at 196, H at 220, and E at 380 positions (see FIG. 4), CaMPARI v1 (also referred to as CaMPARI v1.0) has I at 153, I at 167, V at 196, Y at 220 and M at 380 position as seen in FIG. 6 (and SEQ ID NO:1).

Accordingly, by screening libraries of variants at individual codon positions, variants were identified that improved the fluorescence brightness and/or photoconversion rate difference+/−calcium. Several of these variants were combined to produce CaMPARI v1 (FIG. 6). The amino acid positions changed between CaMPARI v0.1 and CaMPARI v1 are highlighted on the primary and tertiary structure in FIG. 7.

EXAMPLE 2

This Example describes procedures used to determine the crystal structure of the novel fluorescent proteins. The crystal structures of this Example were used to, among other things, identify mutations that may enhance the properties of the fluorescent proteins.

To develop a crystal structure, purified CaMPARI v0.2 (CaMPARI v0.1 with E380M mutation) protein in 10 mM Tris, 100 mM NaCl, 10 mM EGTA was mixed with an equal volume of a precipitant solution of 200 mM ammonium sulfate, 100 mM HEPES pH 7.5, 25% PEG 3350 at room temperature in a sitting-drop vapor diffusion setup. A single yellow-green dagger-shaped crystal was cryoprotected in the precipitant solution supplemented with 20% glycerol, and x-ray diffraction data were collected at 100 K. Data were processed using MOSFLM and SCALA within the CCP4 software package. The structure was solved by molecular replacement searching first for the EosFP fragment using a single EosFP molecule from PDB ID 1ZUX, followed by portions of the CaM domain using a fragment of PDB ID 3EKJ. Iterative model building in Coot and refinement in Refmac led to the model described in Table 1.

Figure 5:
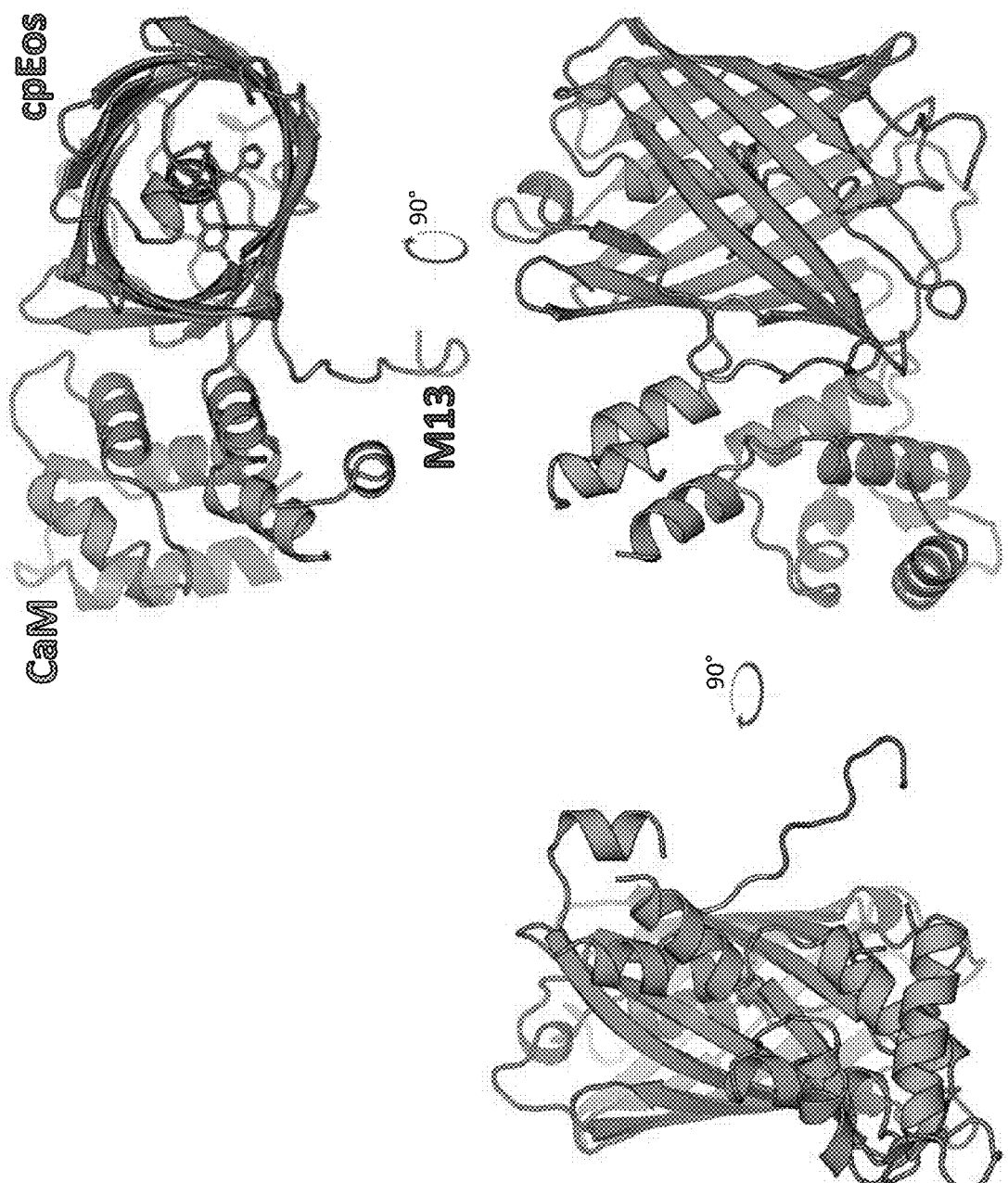
FIG. 5 includes illustrations showing CaMPARI v0.1.

The resulting crystal structure of CaMPARI v0.2 in the absence of calcium is shown in FIG. 5. The structure shows the relative positions of the circularly permuted EosFP (cpEos), CaM, and M13 domains and the interfaces between those domains. This information was used to help target mutagenic libraries for optimization of CaMPARI properties, as described in Example 1.

TABLE 1

X-ray crystallographic data collection and refinement statistics.

| Data Collection | |
| --- | --- |
| Crystal | CaMPARI v0.2 apo |
| Space Group | P4$_1$2$_1$2 |
| Unit Cell Dimensions | |
| a (Å) | 68.7 |
| b (Å) | 68.7 |
| c (Å) | 172.8 |
| X-ray source | ALS 8.2.2 |
| Temperature (K) | 100 |
| Wavelength (Å) | 1.000 |
| Resolution Range (Å) | 69-2.0 |
| Completeness (%) | 99.9 (99.5) |
| Redundancy | 7.5 (6.6) |
| I/σ(I) | 13.4 (4.0) |
| R$_{sym}$ (%) | 9.4 (51.2) |
| Refinement | |
| R$_{cryst}$/R$_{free}$ (%) | 19.2/23.0 |
| Resolution Range (Å) | 54-2.0 |

Numbers in parentheses are for the highest resolution shell data.

EXAMPLE 3

This Example describes procedures performed to characterize the in vitro properties of the fluorescent proteins. First, CaMPARI protein was expressed from the pRSET plasmid (Life Technologies, Carlsbad, Calif.) in T7 Express E. coli cells cultured for 36 h in 100 mL of autoinduction medium supplemented with 100 mg/L ampicillin. Cell pellets were lysed using B-PER (Pierce, Rockford, Ill.) supplemented with 1 mg/mL lysozyme and 1 min. of sonication. After removing insoluble material by centrifugation, CaMPARI protein was purified by immobilized metal affinity chromatograpy on nickel-charged Profinity resin (Bio-Rad, Hercules, Calif.), washing with 10 mM imidazole and eluting with 100 mM imidazole.

Using these samples, calcium titrations were used to calculate an apparent affinity of the protein for calcium ions. Aliquots of purified CaMPARI protein were mixed with Ca-EGTA solutions calculated to contain a range of free $Ca^{2+}$ ions (Life Technologies) and fluorescence was measured in a plate reader. Furthermore, to observe the photoconversion rate difference+/−calcium, purified CaMPARI in 5 mM $CaCl_2$ or 5 mM EGTA were photoconverted using a 400 nm LED array and green and red fluorescence was measured at various time points to fit an exponential rate to the appearance of red fluorescence or the disappearance of green fluorescence.

Figure 8:
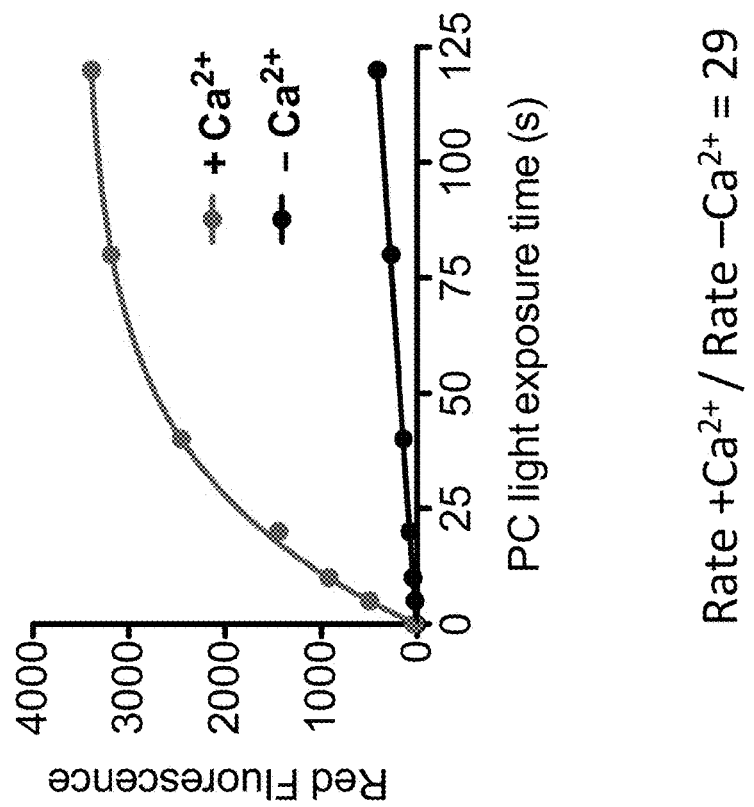
FIG. 8 includes a plot showing the amount of red fluorescence present after exposure to photoconversion light in the presence or absence of calcium as a function of time. Lines are single exponential fits to the data, from which the rates were calculated.
Figure 9:
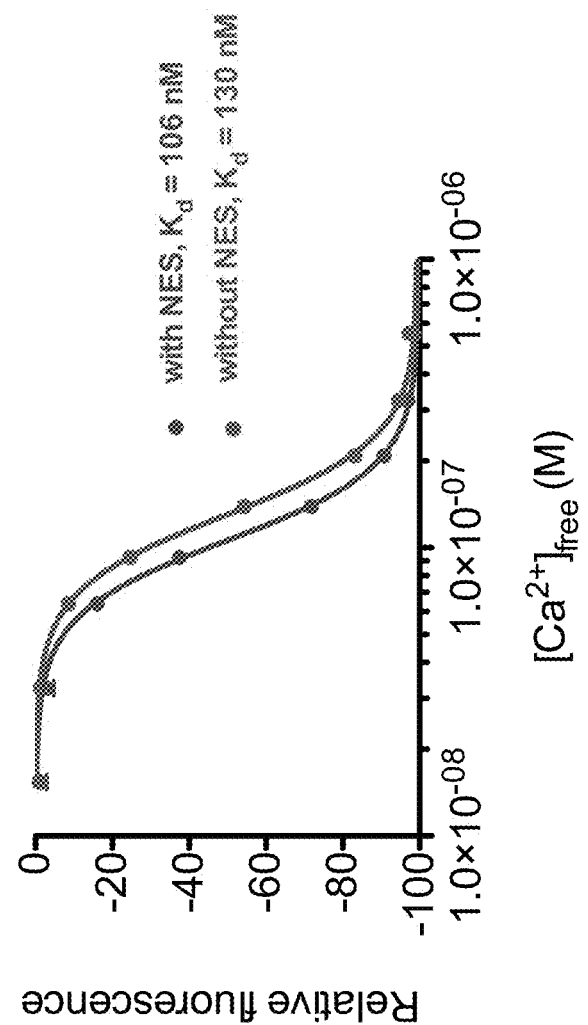
FIG. 9 includes a plot showing the amount of green fluorescence for CaMPARI proteins with or without the N-terminal nuclear export signal (NES) tag as a function of $Ca^{2+}$ concentration in buffer solution. A sigmoidal binding curve was fit to the data to estimate calcium dissociation constants ($K_d$).
Figure 10:
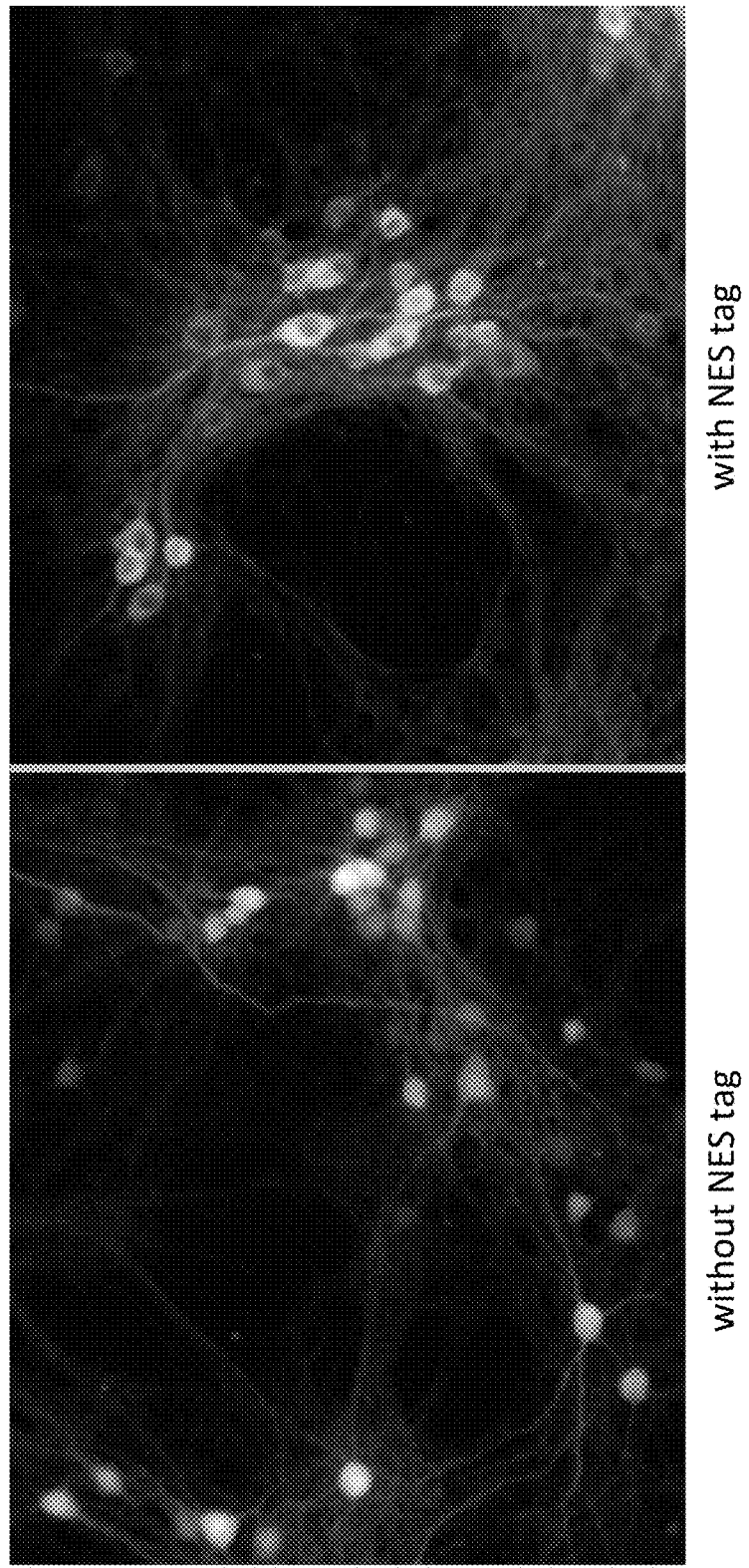
FIG. 10 includes images taken with a epifluorescent microscope (20× objective) showing the expression and nuclear exclusion of CaMPARI without NES (left) and with NES (right) that was delivered to cultured rat hippocampal neurons by lentiviral infection and expressed from the human synapsin promoter.
Figure 11:
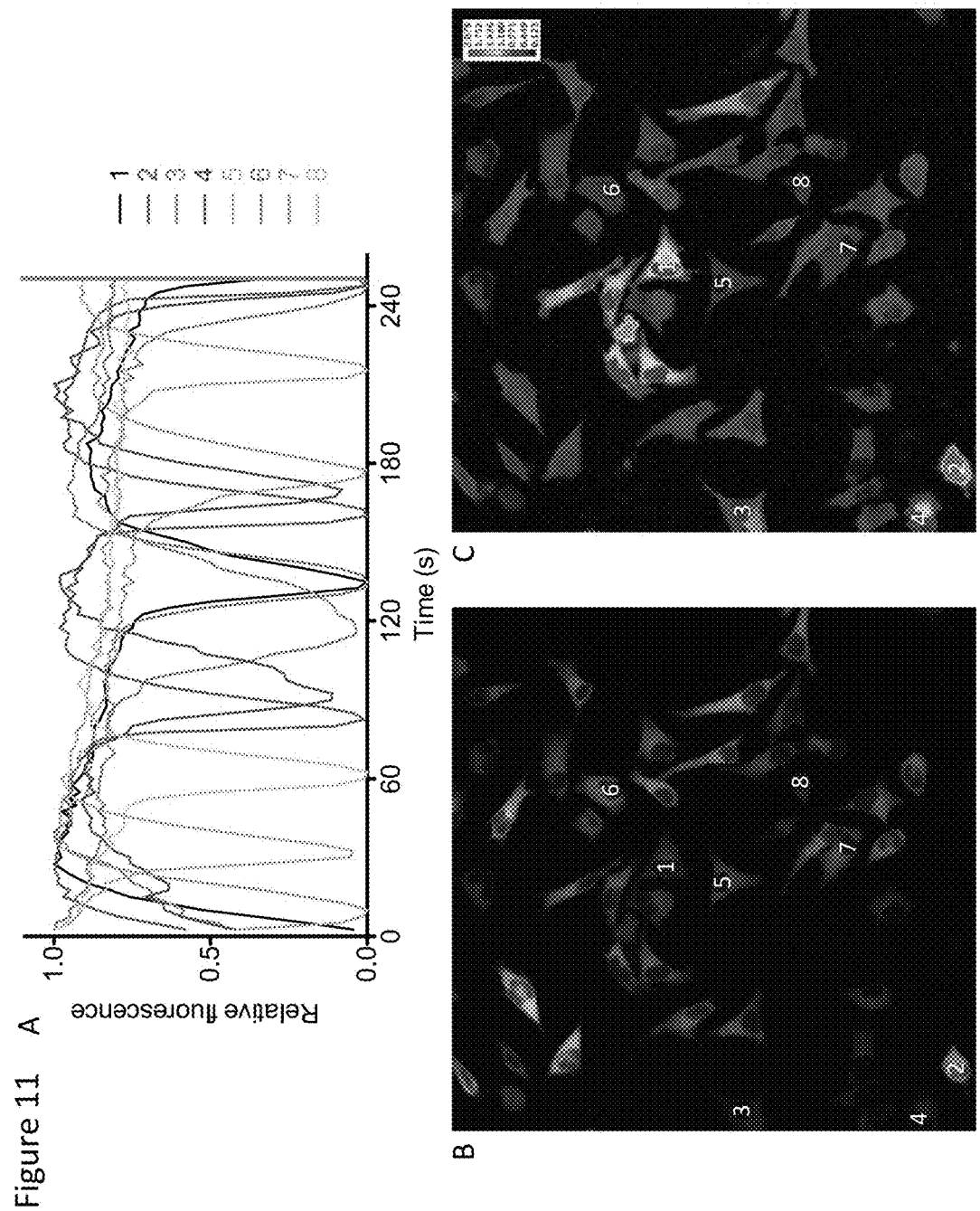
FIG. 11 includes data collected after CaMPARI was delivered to cultured HeLa cells by nucleofection and expressed from the human synapsin promoter, where (A) shows the fluorescence of individual cells oscillating between a low calcium bright state and a high calcium dim state following addition of 1 μM histamine to the culture and delivery of a 2 s pulse of photoconversion light to the culture at the right, vertical bar (numbered traces refer to cells of the same number in B and C), (B) shows a composite image of the red and green fluorescence of the cells following the photoconversion light pulse and removal of calcium with 5 μM ionomycin and 10 mM EGTA, and (C) shows a red/green ratio image of the same field as (B). Cells that underwent more photoconversion (more red, cells 1-4) were each in a high calcium dim state at the time of the photoconversion light pulse; cells that underwent less photoconversion (more green, cells 5-8) were each in a low calcium bright state at the time of the photoconversion light pulse.
Figure 12:
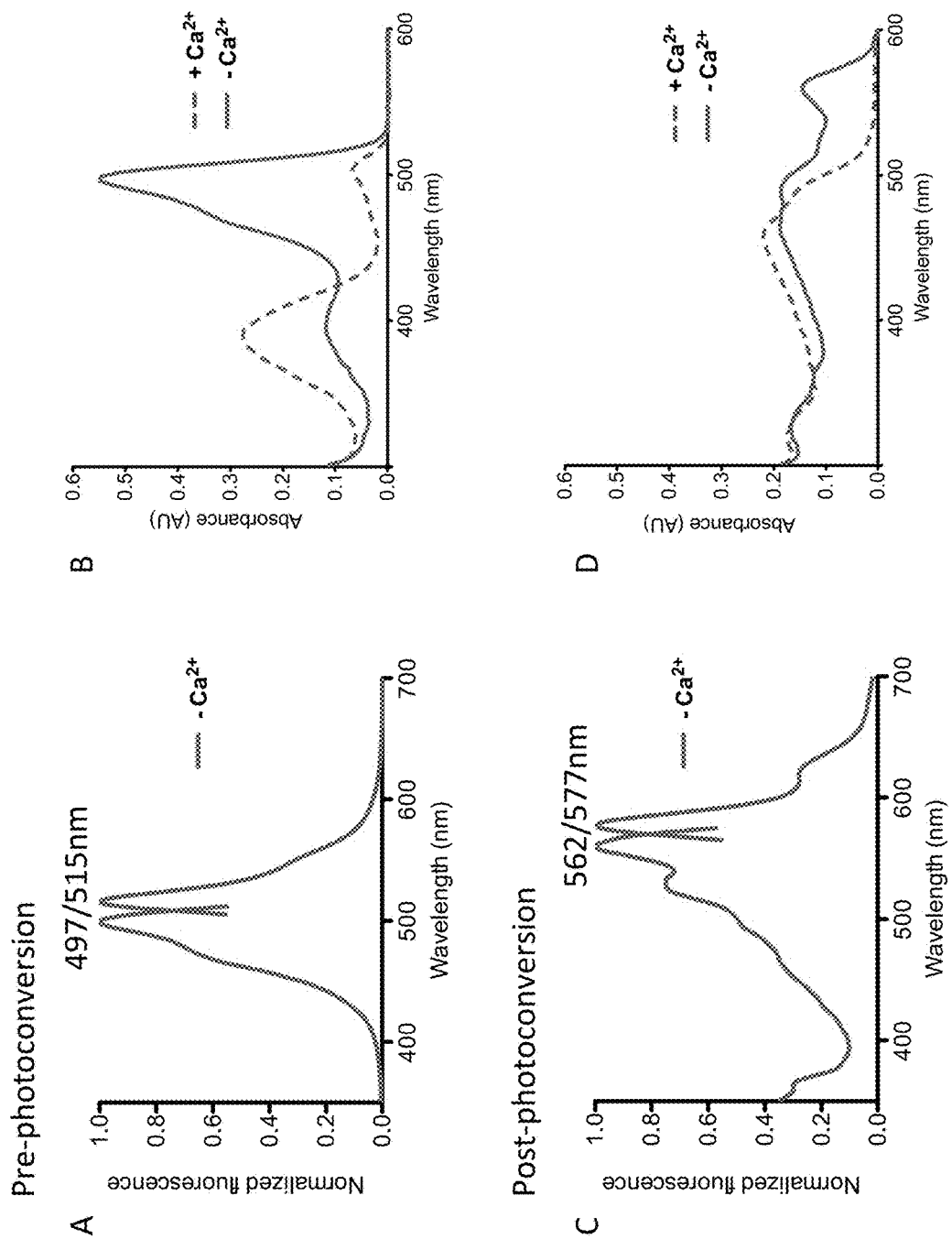
FIG. 12 includes plots showing the fluorescence (A,C) and absorbance (B,D) spectra of purified CaMPARI protein solutions either in the absence of calcium (solid traces) or in the presence of 5 mM calcium (dashed traces), where spectra are shown before any exposure to photoconversion light (A,B) and after extensive exposure to photoconversion light (C,D) (fluorescence excitation and emission maxima indicated in (A,C)).

It was observed that purified CaMPARI v1 protein comprised a 29-fold faster green-to-red photoconversion rate in the presence of calcium (FIG. 8). The green and red forms of CaMPARI were 8-fold and 34-fold less fluorescent, respectively, in the presence of calcium. The fluorescence change with increasing calcium was used to estimate a dissociation constant ($K_d$) of 130 nM (FIG. 9). Addition of the nuclear export signal (NES) MLQNELALKLAGLDINKTG (SEQ ID NO.: 12) to the N-terminus increased the affinity for calcium, with $K_d$=106 nM, and mostly excluded CaMPARI from the nucleus when expressed in either neurons (FIG. 10) or HeLa cells (FIG. 11). The fluorescence excitation and emission spectra were similar to EosFP (FIG. 12). Thus, CaMPARI appeared stable and brightly fluorescent when expressed in multiple eukaryotic cell types (FIGS. 10 and 11).

EXAMPLE 4

This Example describes procedures used to characterize how the novel fluorescent proteins respond in histamine-stimulated HeLa cells. It is known that, in response to extracellular exposure to micromolar concentrations of histamine, HeLa cells undergo large cytoplasmic calcium oscillations. Thus, this Example describes how the novel fluorescent proteins can detect and characterize cytoplasmic calcium oscillations.

HeLa cells were nucleofected with plasmids allowing expression of CaMPARI and plated on glass-bottom dishes. 48 h after nucleofection, CaMPARI-expressing HeLa cells were washed three times with HBSS containing 20 mM MOPS, pH 7.2. Histamine (final conc 5 µM) was then added and green fluorescence was imaged at 1 Hz using a 20× objective. A 1 s pulse of photoconversion light was delivered through the 20× objective about 4 min after addition of histamine. The green and red fluorescence was imaged after photoconversion. All epifluorescence imaging and photoconversion in HeLa cells and cultured neurons was done using a mercury lamp with the following filter combinations. Green fluorescence: excitation=475/23 nm, dichroic mirror=495 nm, emission=511/20 nm; red fluorescence: excitation=555/20 nm, dichroic mirror=561 nm, emission=612/69 nm; photoconversion: excitation=440 nm/SP, dichroic mirror=580 nm.

It was observed that addition of 1 µM histamine to HeLa cells expressing CaMPARI induced periodic, transient decreases in green fluorescence from the cells (FIG. 11A), consistent with the observed decreased fluorescence of the purified protein upon addition of calcium. Exposure to a 2 s pulse (4 W/cm$^2$) of photoconversion light during histamine-induced calcium oscillations followed by imaging of the cells in the red and green fluorescence channels after removal of calcium with ionomycin/EGTA revealed a wide range in the extent of photoconversion, seen in either the composite image of red and green fluorescence or the red/green ratio. The extent of photoconversion in each HeLa cell correlated with the green fluorescence brightness (i.e., intracellular calcium concentration) immediately prior to the photoconversion pulse. Cells that were near the peak of a calcium oscillation (cells 1-4 in FIG. 11) underwent more green-to-red photoconversion and appeared more red (FIG. 11B), while cells that were closer to the low baseline intracellular calcium concentration (cells 5-8 in FIG. 11) photoconverted less and appeared more green (FIG. 11B).

EXAMPLE 5

This Example describes procedures conducted on cultured rat hippocampal neurons and that are intended to further characterize the novel fluorescent proteins. In particular, this Example describes the response of the proteins in cultured neurons to electric field-stimulations as well as the effects that fixation have on the proteins' fluorescent signals.

First, cultured rat hippocampal neurons were prepared and infected with lentivirus expressing CaMPARI from the human synapsin promoter. The neurons were imaged ten days after infection with a 10× objective before and after various combinations of photoconversion and field electrode-induced action potential firing. Prior to imaging, the neuron cultures were washed with imaging buffer and spontaneous activity was blocked with a drug mix.

Figure 13:
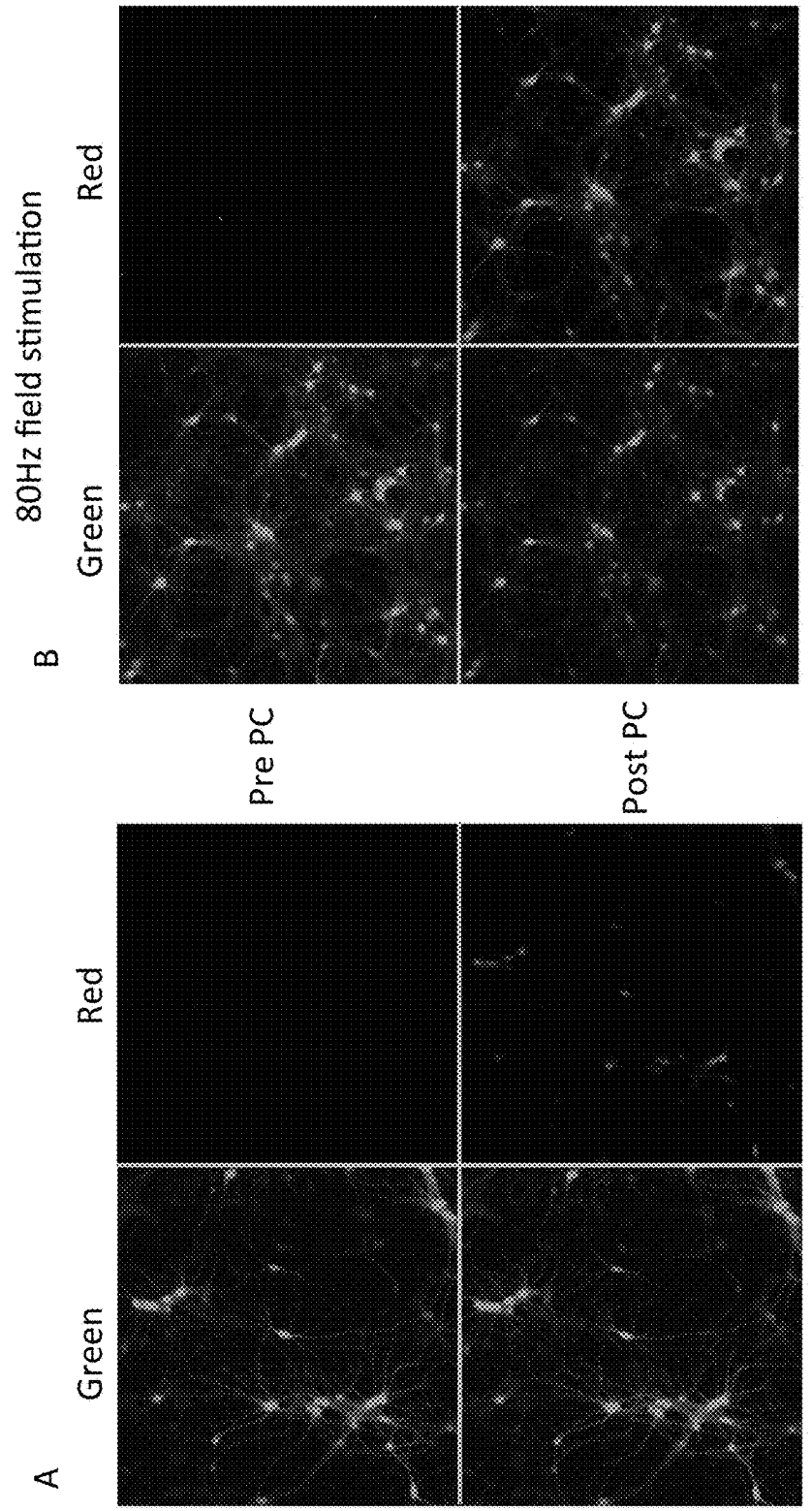
FIG. 13 includes images showing (A) cultured rat hippocampal neurons expressing CaMPARI both before (top) and after (bottom) exposure to 2 s of photoconversion light, and (B) same as panel (A) with the addition of 80 Hz electrical field stimulation to induce high-frequency action potential firing.
Figure 14:
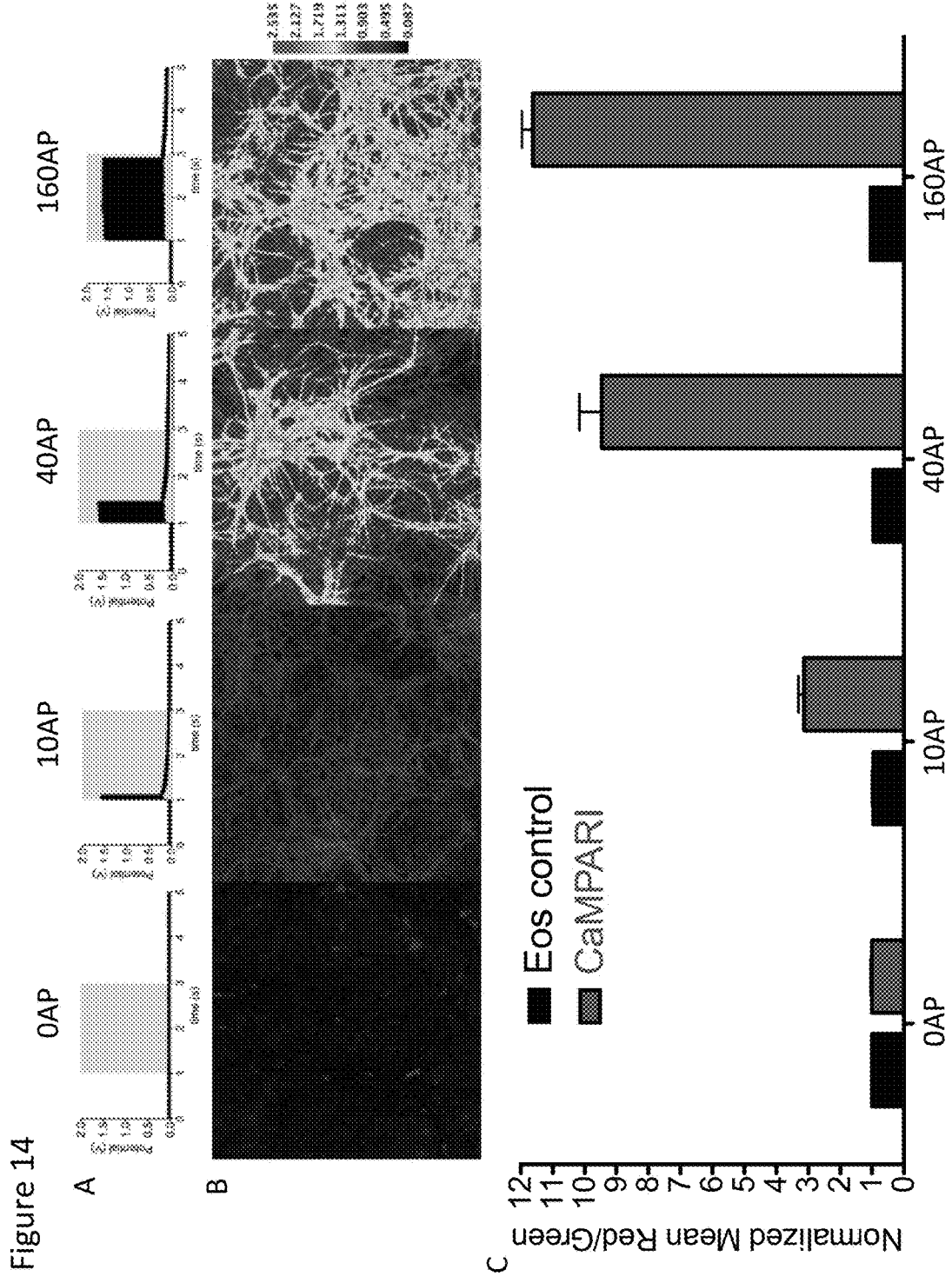
FIG. 14 includes plots and images showing (A) a protocol for exposing cultured rat hippocampal neurons expressing CaMPARI to 2 s photoconversion light pulses (shaded box) accompanied by 83 Hz action potential (AP) trains of different lengths (black traces), (B) the red/green ratio of the neuron fluorescence imaged after the various photoconversion/field stimulation pulses shown in (A), and (C) a quantification of the red/green signal within neurons following the various photoconversion/field stimulation pulses shown in (A), normalized to the response at 0 AP, for both CaMPARI and the parent EosFP variant control.
Figure 15:
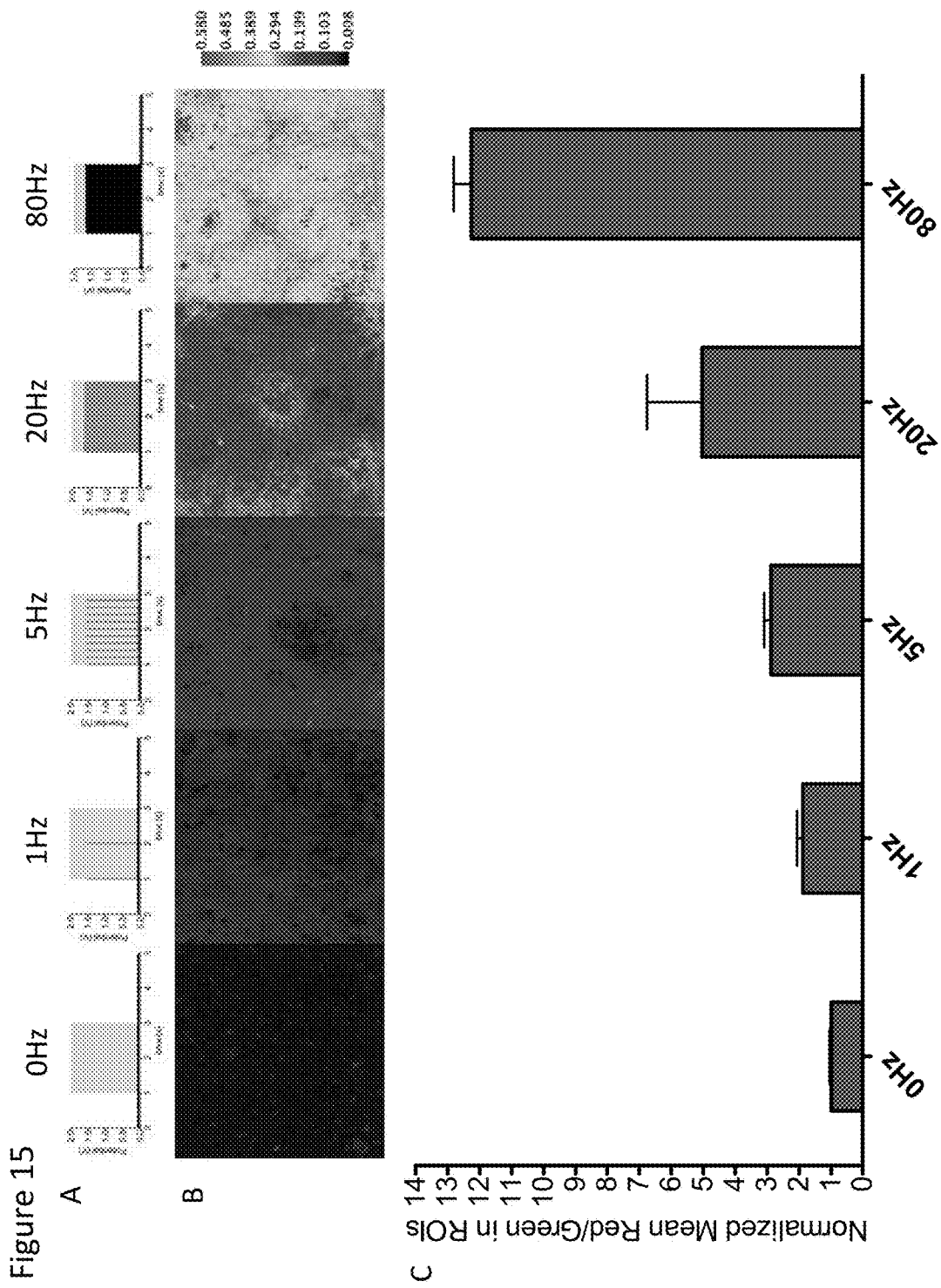
FIG. 15 includes plots and images showing (A) a protocol for exposing cultured rat hippocampal neurons expressing CaMPARI were exposed to 2 s photoconversion light pulses (shaded box) accompanied by action potential (AP) trains of different frequencies (black traces), (B) the red/green ratio images of the neuron fluorescence imaged after the various photoconversion/field stimulation pulses shown in (A), and (C) a quantification of the red/green signal within neurons following the various photoconversion/field stimulation pulses shown in (A), normalized to the response at 0 Hz.
Figure 16:
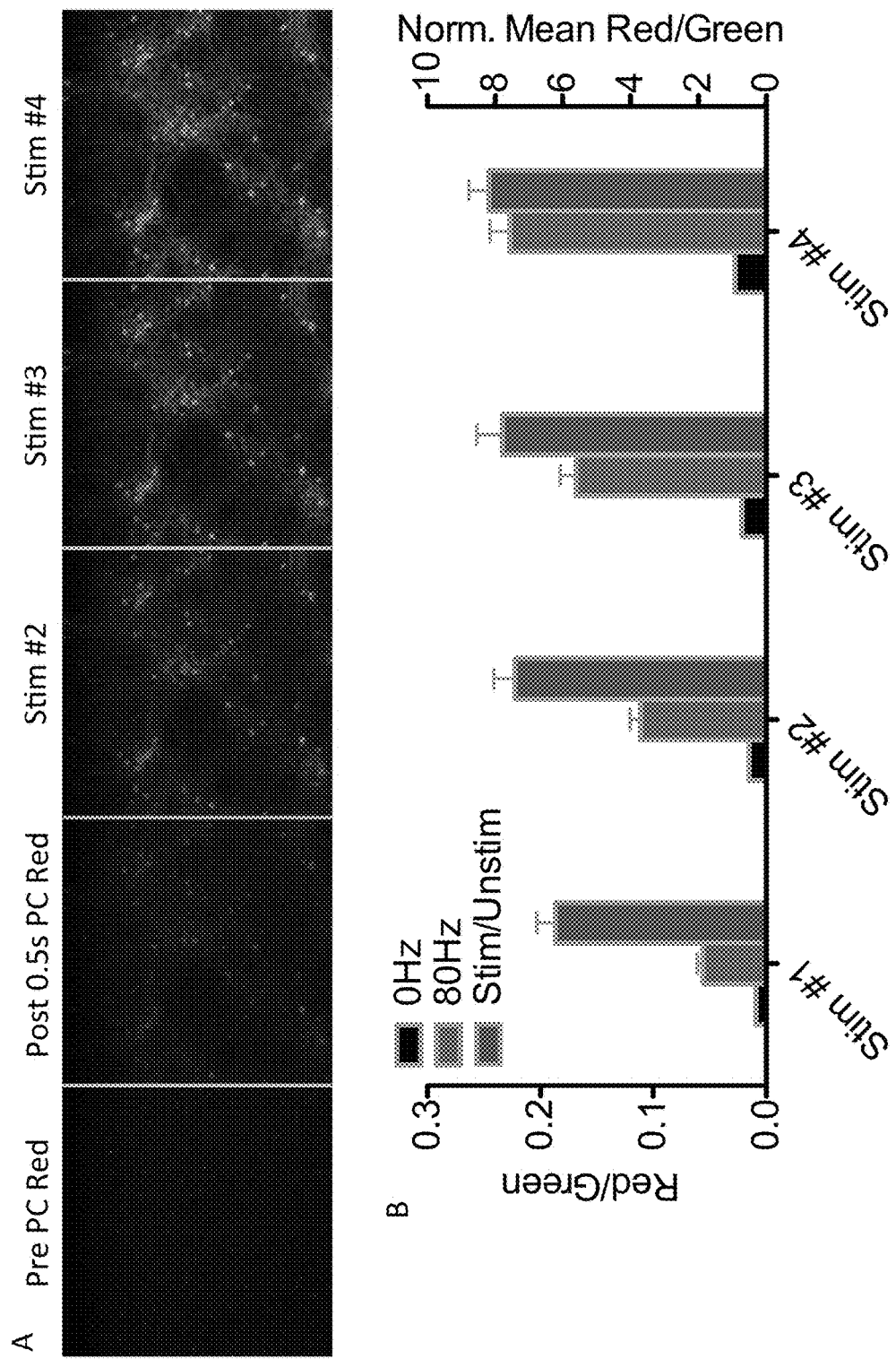
FIG. 16 includes (A) images showing the red fluorescence acquired after exposing cultured rat hippocampal neurons expressing CaMPARI to each of four consecutive pulses of 0.5 s of photoconversion light accompanied by 80 Hz field stimulation, and (B) a plot showing the red/green ratio in neurons following each light pulse accompanied by either no field stimulation or 80 Hz field stimulation (left Y-axis, two left bars) and the ratio of 80 Hz/0 Hz signal after each pulse (right Y-axis, right bar).
Figure 17:
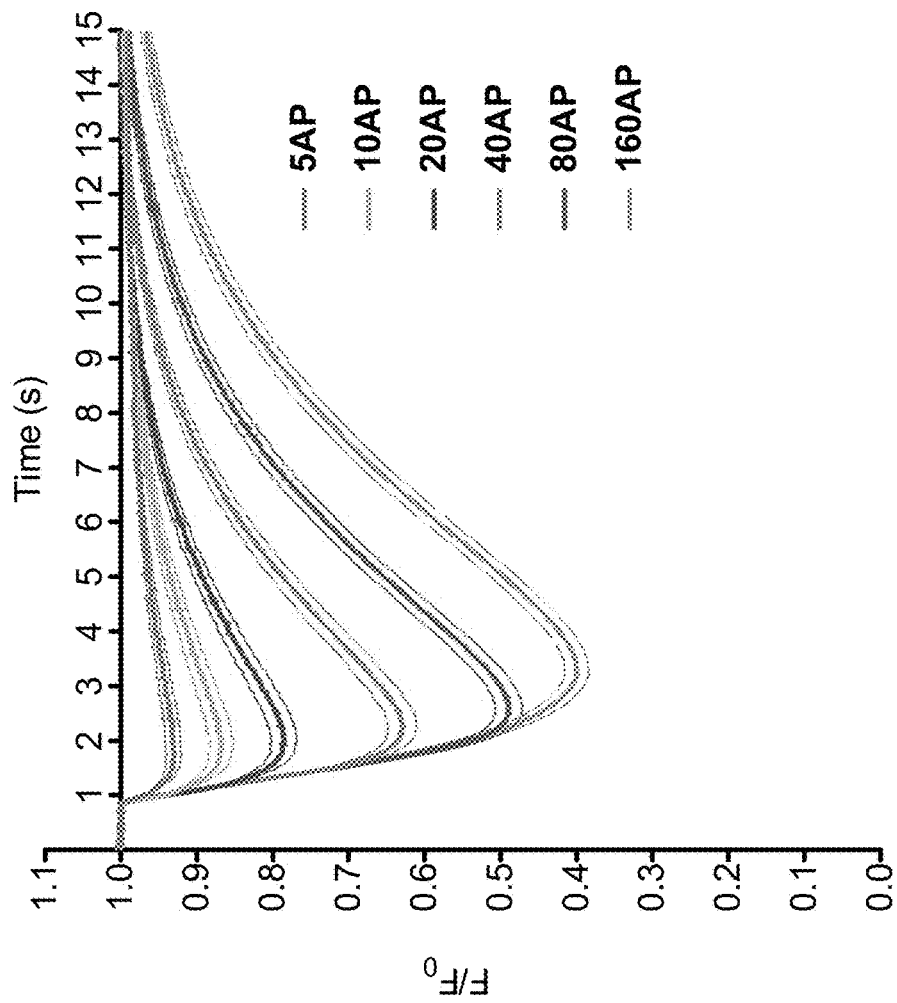
FIG. 17 includes a plot showing the average and standard deviation green fluorescence after exposing cultured rat hippocampal neurons expressing CaMPARI to 83 Hz action potential (AP) trains of different lengths induced by field stimulation during simultaneous epifluorescence imaging of the green fluorescence signal (F, fluorescence at a given time; $F_0$, fluorescence during the 1 s prior to field stimulation).

The imaging showed that the CaMPARI expressed in primary rat hippocampal neurons in culture exhibited bright green fluorescence (FIG. 13) and did not exhibit visible red fluorescence. Following a 2 s pulse of photoconversion light (1.5 W/cm$^2$) to CaMPARI-expressing neurons, there was no significant decrease in green fluorescence and a small amount of red fluorescence was visible (FIG. 13A). Following application of the same dose of photoconversion light concurrent with field electrode stimulation of the neurons to induce action potential firing at 80 Hz, a significant decrease in green fluorescence and a brighter red signal was observed in the neurons (FIG. 13B). Stimulation of 0, 10, 40, or 160 action potentials (83 Hz) at the beginning of a 2 s photoconversion pulse (FIG. 14A) produced increasing amounts of green-to-red photoconversion (FIG. 14B), up to 12-fold more for 160 action potentials relative to 0 (FIG. 14C). No effect of field electrode stimulation on photoconversion was observed for the parent EosFP variant (FIG. 14C). Similarly, increasing frequencies of field electrode stimulation during photoconversion light exposure (FIG. 15A) produced increasing amounts of green-to-red photoconversion (FIGS. 15B and 15C). Repeated exposures of CaMPARI-expressing neurons to shorter photoconversion light pulses (0.5 s) led to increasing amounts of red fluorescence signal (FIG. 16A) and red/green ratio (two left bars in FIG. 16B), but the ratio of red-to-green photoconversion between 80 Hz field stimulated and unstimulated neurons remained approximately constant (right-most bars in FIG. 16B). Field electrode stimulation of CaMPARI-expressing neurons (without application of photoconversion light) led to transient decreases in the green fluorescence signal, proportional to the number of induced action potentials (FIG. 17).

Also, as stated above, the fluorescent signals were observed after fixing the neurons, particularly since it is known that fixation may also alter the CaMPARI signal after photoconversion and prior to imaging. Of course, cell or tissue fixation protocols are often used to halt physiological processes in cells, such as protein translation or degradation. Fixation additionally allows for antibody staining of cells.

Figure 18:
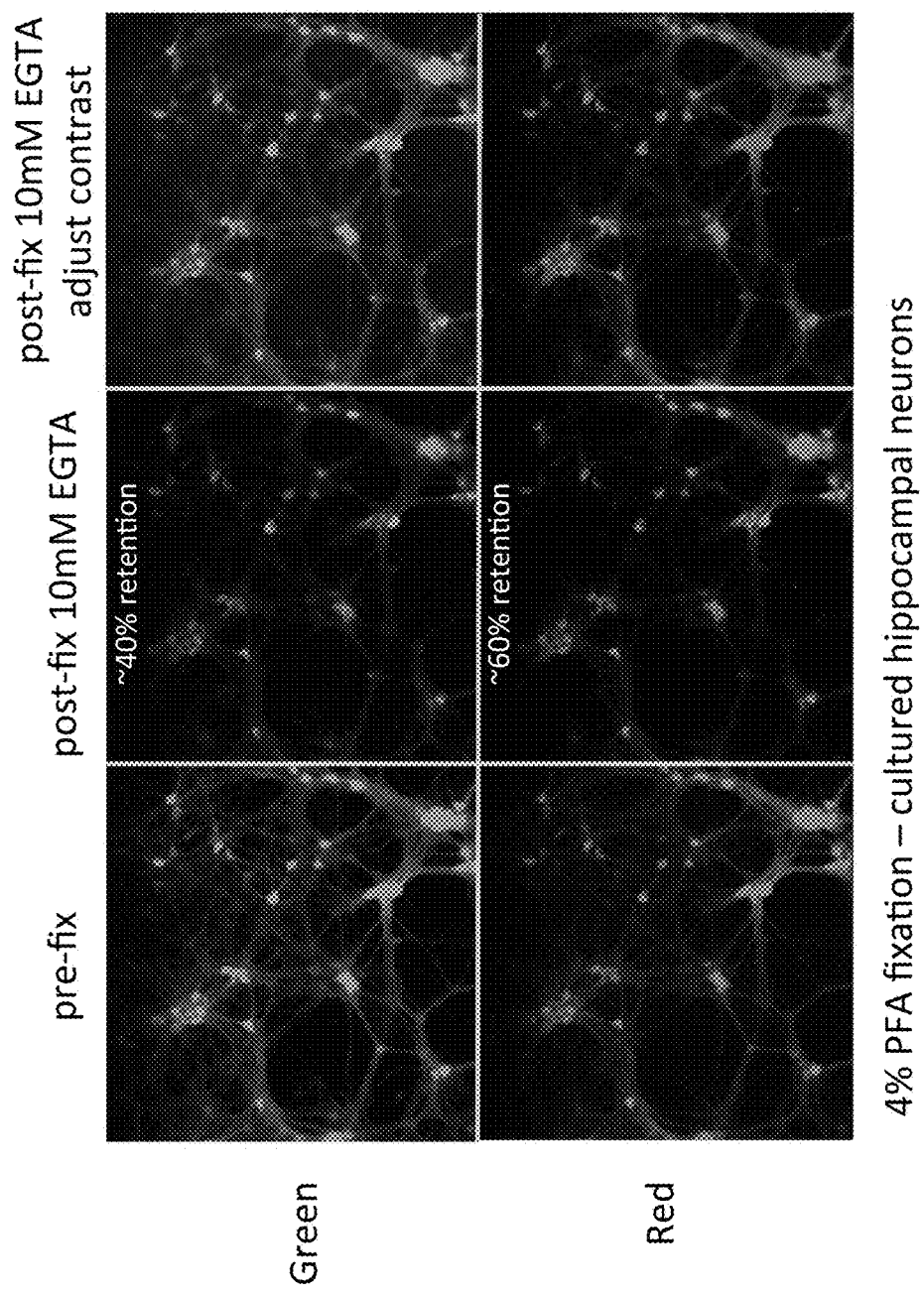
FIG. 18 includes images showing cultured rat hippocampal neurons expressing CaMPARI that were partially photoconverted to allow observation of both the green (left, top) and red (left, bottom) fluorescence (left-panels), the neurons after being fixed with a standard 4% paraformaldehyde (PFA) fixation protocol (center-panels), and the neurons after fixation being contrast adjusted to better resemble the pre-fixation images (right panels).

To test the CaMPARI samples, cultured rat hippocampal neurons expressing CaMPARI were partially photoconverted and then fixed using a standard 4% paraformaldehyde protocol. When 10 mM EGTA was included in the washes following fixation, 40% and 60% of the endogenous CaMPARI green and red fluorescence signal, respectively, were retained relative to images taken before fixation (FIG. 18). Inclusion of 10 mM EGTA helped remove calcium so that CaMPARI was in a brighter, calcium-free state, and helped ensure that all cells were imaged at an equivalent level of intracellular calcium. Adjusting the contrast of the post-fixation fluorescence images showed that little to no details of the fluorescence signal, such as visibility of neurites, were lost following fixation (FIG. 18, right panel).

EXAMPLE 6

This Example describes procedures used to characterize the novel fluorescent proteins in vivo. In particular, this Example describes properties of CaMPARI that has been transgenically delivered to a mouse and is expressed in the cortical neurons.

To transgenically deliver CaMPARI, a pregnant mouse (E16) was deeply anesthetized with isoflurane (2%). Then, the uterine horns were surgically exposed and plasmid DNA (5 mg/ml) mixed with 0.03% Fast Green dye in phosphate buffer was injected into the ventricle of embryos through a micropipette (~0.1 µL per embryo). Electroporation was done using custom forceps electrodes (5 pulses, 100 ms, 40 V). Additionally, 30 nL volumes of adeno-associated virus (AAV) particles in saline solution were stereotactically injected into the V1 region of another anesthetized mouse's visual cortex through the thinned skull of the mouse.

Figure 19:
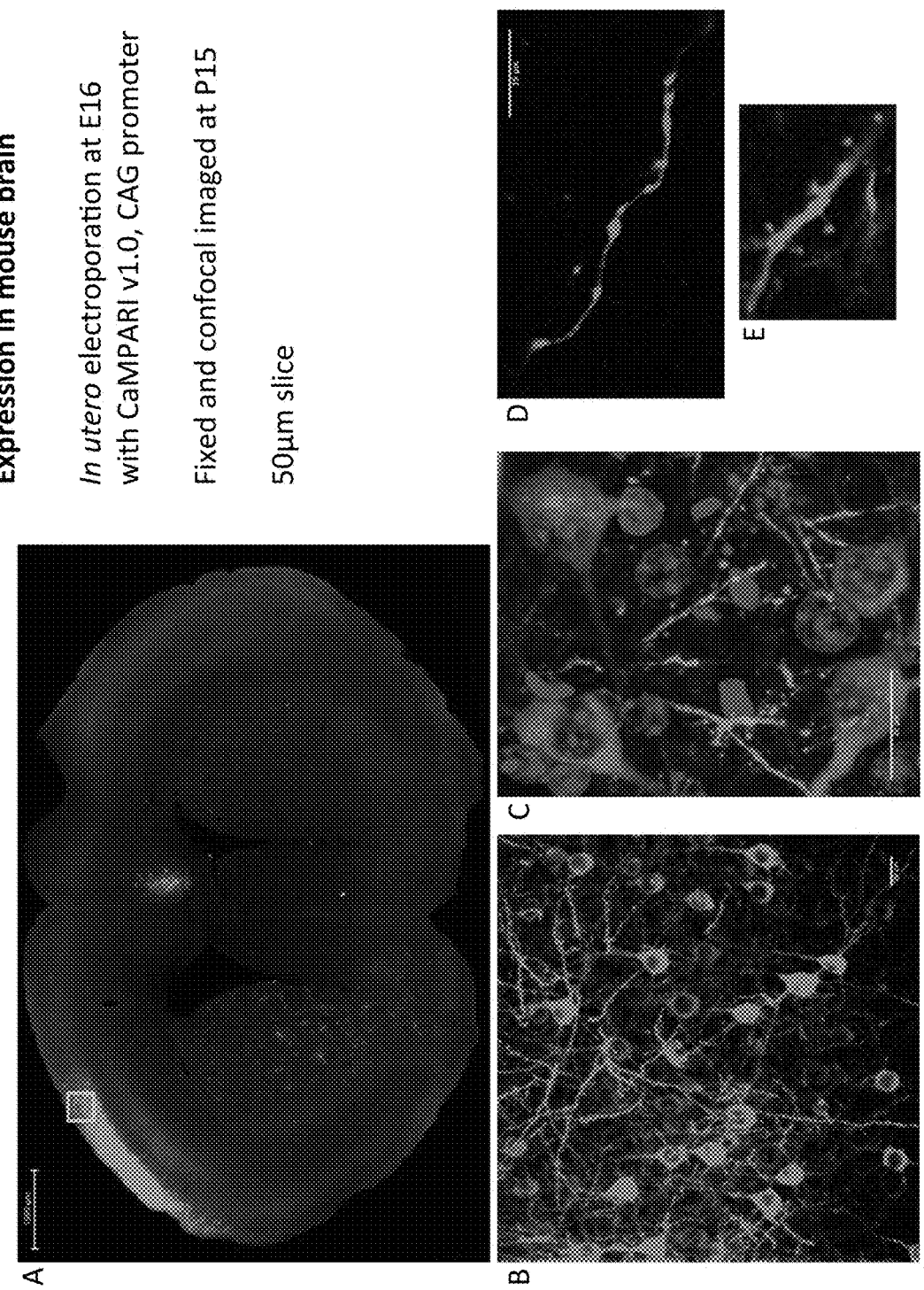
FIG. 19 includes images showing (A) a slide scanner image of green fluorescence from CaMPARI in a fixed 50 μM slice of mouse brain expressing CaMPARI from the CAG promoter two weeks after birth following in utero electroporation at E16, (B) a green fluorescence confocal microscopy image of the boxed region in (A) showing cell bodies of layer 2/3 cortical neurons and processes, (C) a higher magnification green fluorescence confocal microscopy image of layer 2/3 cortical cell bodies, (D) a portion of a labeled axon with bouton structures, and (E) a portion of a labeled dendrite with spine structures.
Figure 20:
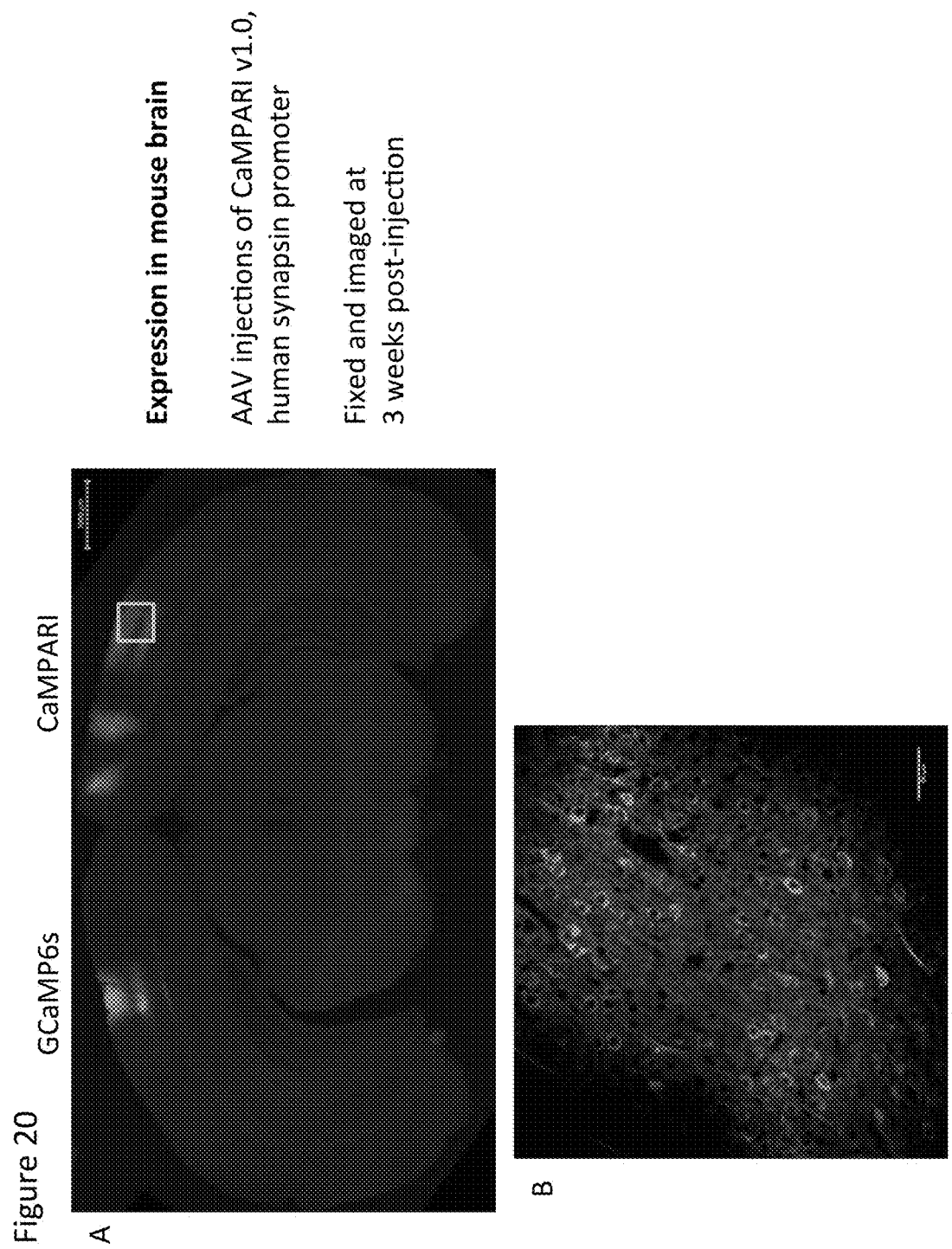
FIG. 20 includes images showing (A) a slide scanner image of green fluorescence from CaMPARI in a fixed 50 μM slice of mouse brain expressing CaMPARI from the human synapsin promoter three weeks after injection of adeno-associated virus (AAV), where three distinct AAV-CaMPARI injection sites are visible on the right side and one AAV-GCaMP injection site is visible on the left side for reference, and (B) a green fluorescence confocal microscopy image of the boxed region in (A) showing cell bodies of layer 2/3 (top right) and layer 5 (bottom left) cortical neurons

CaMPARI was expressed in cortical neurons of mouse brains after transgene delivery by either in utero electroporation (FIG. 19) or injection of AAV (FIG. 20). Green CaMPARI fluorescence was bright when imaging fixed sections using confocal microscopy. The fluorescence signal appeared evenly distributed throughout the cell bodies, with no punctate labeling indicative of aggregation (FIGS. 19B, 19C, and 20B). Fine structures such as axonal boutons and dendritic spines were also visible (FIGS. 19D and 19E). Thus, CaMPARI served as a viable indicator after transgenic delivery.

EXAMPLE 7

This example describes the preparation of adenoviral vector comprising a polynucleotide encoding a PAM. The adenoviral vector was obtained through the Vector Development Lab at Baylor College of Medicine. Briefly, the CaMPARI gene was cloned into pShuttle plasmid, which was then used to clone it into the adenovirus backbone plasmid. Cells were transfected with the plasmid and plaques grown. Plaques were selected, expanded and cell lysates were tested for transgene expression. The virus produced was purified using cesium chloride gradient ultracentrifugation.

EXAMPLE 8

Figure 21:
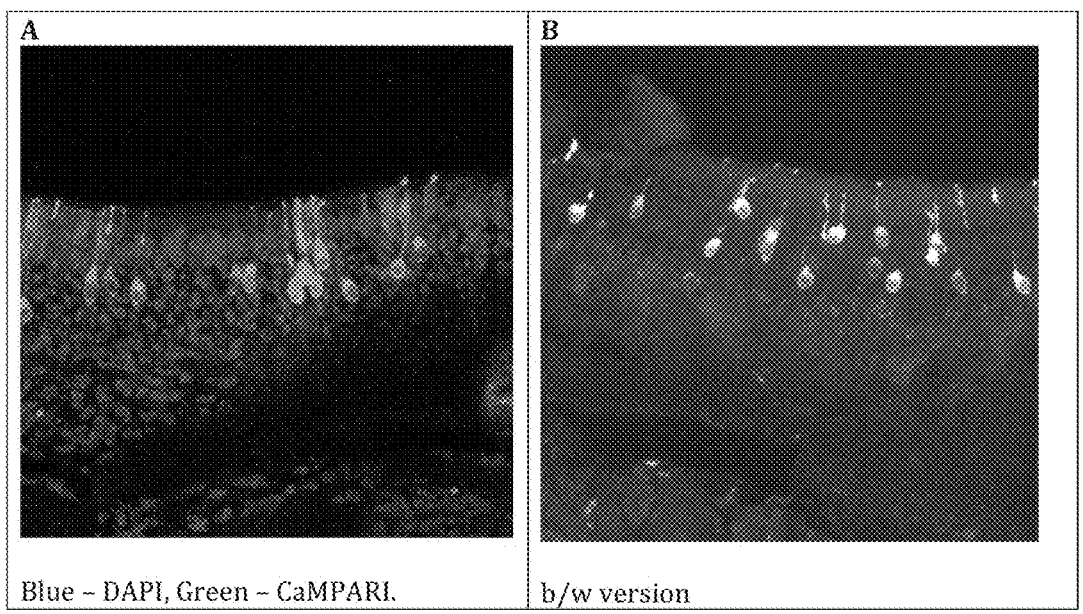
FIG. 21 is an image showing the expression of CaMPARI v1.0 in OSNs in the nasal epithelium of mice following adenoviral infection. A is a color image while B is a black & white image of a different section of the epithelium.

This example describes the use of the adenoviral vector from Example 7 to effect expression of a PAM in vivo. Viral infection was performed by perfusing 10 µl of lysate (concentration approximately 10^8 pfu) into naris of an anesthetized adult C57BL/6J mouse. Infection protocol was preformed two times at 24 hr interval. At 72 hours post infection, animal was sacrificed and the nasal epithelium was extracted and fixed in 4% paraformaldehyde solution in phosphate buffered saline for 10 hrs. Following fixation, epithelium was decalcified in 0.5 M EDTA for 12 hrs, followed by 10 mM EGTA calcium chelation for 12 hrs. Samples were flash frozen using dry ice and cut into 18 um-thick sections in cryostat microtome. CaMPARI v 1.0 expression was visualized using Carl Zeiss LSM 510 scanning confocal microscope using 488 nm excitation line, 505-530 band pass emission filter and 40× Carl Zeiss Plan-Neofluar objective (FIG. 21). Expression of the fluorescent protein in cells with morphology consistent with OSN cell type demonstrates that adenoviral vector induces CaMPARI expression in OSNs within the olfactory epithelium.

EXAMPLE 9

Figure 22:
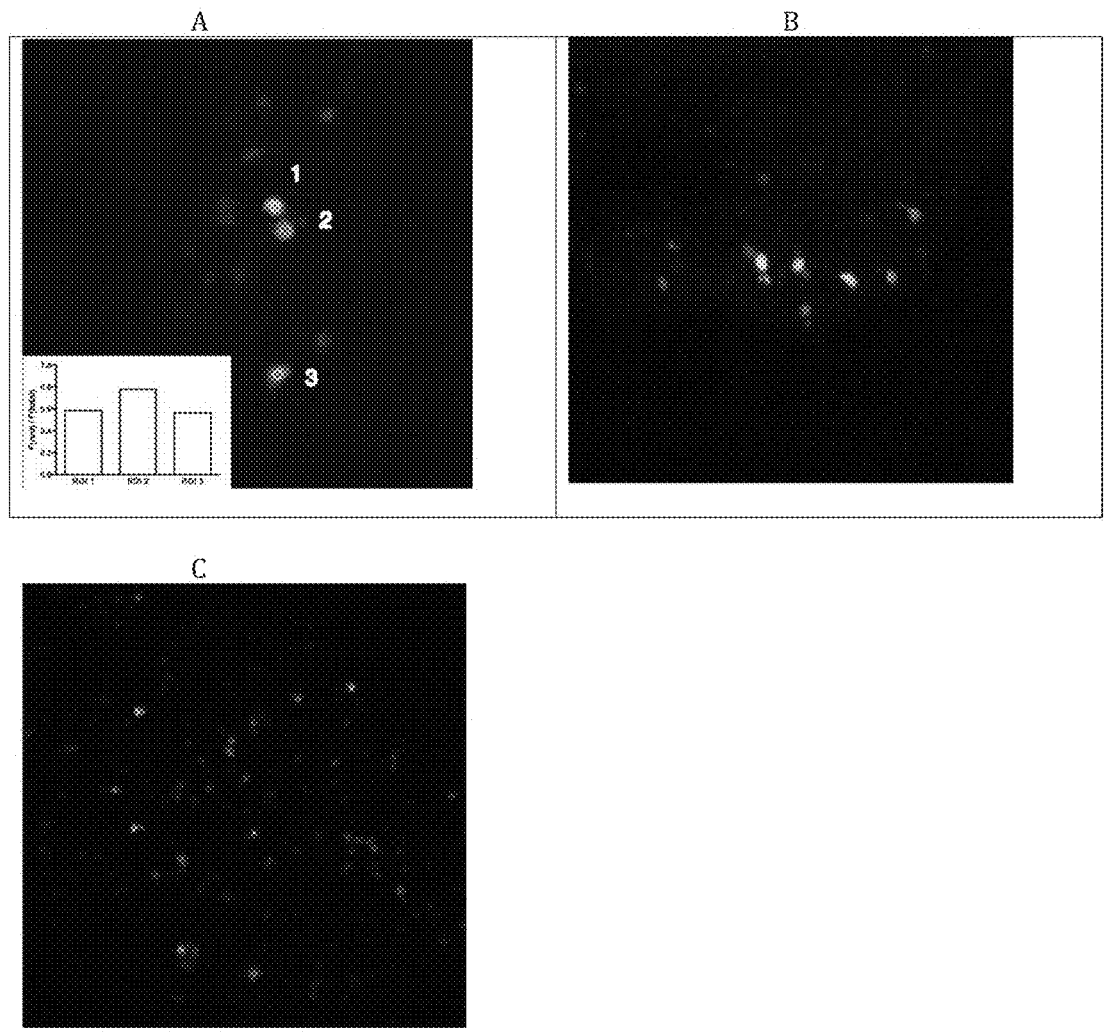
FIG. 22 includes images showing fluorescence of OSNs in the nasal epithelium of mice following introduction of CaMPARI and exposure to an odorant and light. Some cells are seen as green, some as red, and some exhibit mixed fluorescence (yellow). In (A), the ratios of red to green fluorescence are shown for the numbered cells within the inset bar diagram. Figures (B) and (C) also provide examples of cells showing green, red, and mixed yellow fluorescence.

This example demonstrates the expression of PAM in vivo and the use of differential photo conversion ratios following odor and light exposure. Seventy-two hours following infection with CaMPARI v1.0 (W391L) animals were anesthetized using urethane to maintain high breathing rate. Nasal bone was exposed and a small hole was drilled in the caudal nasal bone using a carbide ½ FG dental drill bit to expose surface of nasal epithelium. Photoconversion light was delivered to the epithelium using a 400 um-diameter core fiber with a numeric aperture of 0.39 attached to a 385 nm LED light source (light intensity=30.8 mw/mm^2 at fiber end). Odor and light co-presented under computer control in 100 trials of 5 seconds each with a 20-25 second inter-trial interval. Odors used were: ethyl-tiglate, eugenol, pinene, acetophenone, 4-methylacetophenone, and butyric acid. Following exposure paradigm animals were sacrificed and epithelium removed for imaging. Imaging was performed using Carl Zeiss LSM 510 META confocal microscope with 20× Plan-Apochromat objective. For green channel, 488 nm excitation line and BP505-530 emission filters were used and for red channel, 543 nm excitation line and BP560-615 emission filter was used. FIG. 22. Differential photoconversion rates were observed in cells within close proximity, indicating 1) that CaMPARI photoconversion occurs in OSNs.

EXAMPLE 10

Other CaMPARI variants were constructed and there include V398L, W391F+V398L, W391F, W391L, V398T, G395D, W391Y, W391Y+V398T, V398D, W391F+G395D, W391F+V398H. The variants were made based on substitutions within the M13 domain of CaMPARI that alter the affinity, cooperativity and kinetics and calcium binding. The magnitude of fluorescence change was similar for all variants. Dissociation constants for calcium ($K_d$) and Hill coefficients were determined from a sigmoidal fit to calcium titration data. Kinetics of fluorescence decay upon calcium release were determined by rapid mixing with EGTA in a stopped-flow device. The results are shown in Table 2.

TABLE 2

| Variant | $K_d$ (nM) | Hill | $k_{off}$ (s$^{-1}$) |
| --- | --- | --- | --- |
| V398L | 74 | 2.7 | 0.35 |
| CaMPARI 1.0 | 111 | 2.9 | 0.25 |
| W391F + V398L | 203 | 3.4 | 1.01 |
| W391F | 212 | 2.6 | 0.67 |
| W391L | 397 | 3.6 | 1.99 |
| V398T | 463 | 2.6 | 0.46 |
| G395D | 506 | 2.3 | 0.61 |
| W391Y | 629 | 2.4 | 1.98 |
| W391F + V398T | 736 | 2.2 | 2.50 |
| V398D | 761 | 1.6 | 0.68 |
| W391F + G395D | 1001 | 2.4 | 3.14 |
| W391F + V398H | 1282 | 2.3 | 2.49 |

Throughout this document, various references are mentioned. All such references are incorporated herein by reference, including the references set forth in the following list:

REFERENCES

1. Wiedenmann, J., Ivanchenko, S., Oswald, F., Schmitt, F., Rocker, C. et al. EosFP, a fluorescent marker protein with UV-inducible green-to-red fluorescence conversion. *Proc Natl Acad Sci USA* 101, 15905-15910 (2004).
2. Ando, R., Hama, H., Yamamoto-Hino, M., Mizuno, H. & Miyawaki, A. An optical marker based on the UV-induced green-to-red photoconversion of a fluorescent protein. *Proc Natl Acad Sci USA* 99, 12651-12656 (2002).
3. Baird, G. S., Zacharias, D. A. & Tsien, R. Y. Circular permutation and receptor insertion within green fluorescent proteins. *Proc Natl Acad Sci USA* 96, 11241-11246 (1999).
4. McKinney, S. A., Murphy, C. S., Hazelwood, K. L., Davidson, M. W. & Looger, L. L. A bright and photostable photoconvertible fluorescent protein. *Nat Methods* 6, 131-133 (2009).
5. Akerboom, J., Chen, T. W., Wardill, T. J., Tian, L., Marvin, J. S. et al. Optimization of a GCaMP calcium indicator for neural activity imaging. *J Neurosci* 32, 13819-13840 (2012).
6. Thorn, P. Ca2+ influx during agonist and Ins(2,4,5)P3-evoked Ca2+ oscillations in HeLa epithelial cells. *J Physiol* 482 (Pt 2), 275-281 (1995).

It will be understood that various details of the presently disclosed subject matter can be changed without departing from the scope of the subject matter disclosed herein.

The invention claimed is:

1. A method for identification of olfactory sensory neurons (OSN) that recognize an odorant comprising the steps of:
   a) providing a population of OSNs, each OSN expressing an olfactory receptor (OR) and a permanent activity marker (PAM), wherein the PAM has been introduced into the OSN and exhibits a permanent and detectable change upon activation of the OSN in response to an odorant and exposure to an external stimulus, wherein the external stimulus is light, wherein the PAM comprises:
   an EosFP polypeptide, which includes a C-terminus portion comprising the sequence of SEQ ID NO:2 and an N-terminus portion comprising the sequence of SEQ ID NO:3;
   a calmodulin (CaM) polypeptide, comprising the sequence of SEQ ID NO:4; and
   a M13 polypeptide, comprising the sequence of SEQ ID NO:5 or a variant thereof, wherein the variant is a change in SEQ ID NO: 5 of:
      i) valine at position 13 to leucine, threonine, or aspartic acid,
      ii) tryptophan at position 6 to phenylalanine, leucine, or tyrosine,
      iii) glycine at position 10 to aspartic acid,
      iv) tryptophan at position 6 to phenylalanine and valine at position 13 to leucine,
      v) tryptophan at position 6 to tyrosine and valine at position 13 to threonine,
      vi) tryptophan at position 6 to phenylalanine and glycine at position 10 to aspartic acid: or
      vii) tryptophan at position 6 to phenylalanine and valine at position 13 to histidine;
   b) exposing the population of OSNs to a test odorant and the external stimulus that will cause the PAM to exhibit the detectable change if the OSN containing the PAM is activated in response to the odorant;
   c) isolating the OSNs exhibiting the detectable change in PAM from the OSNs that do not exhibit the detectable change in PAM; and
   d) identifying the OR or ORs expressed in the isolated OSNs.

2. The method of claim 1, wherein the PAM is a fluorescent protein which fluoresces or changes its fluorescence when exposed to light that comprises a wavelength of about 340 nm to about 420 nm.

3. The method of claim 2, wherein the OSNs in step c) are isolated by fluorescence activated cell sorting.

4. The method of claim 1, wherein the detectable change in step b) is a color shift of a fluorescence emitted by the isolated polypeptide from green to red, an increase in brightness of the fluorescence, an increase in a red-to-green ratio of the fluorescence, or a combination thereof.

5. The method of claim 4, wherein the detectable change is normalized against the amount of light delivered to the OSN.

6. The method of claim 1, wherein the external stimulus is applied from 0.01 milliseconds to 10 minutes.

7. The method of claim 1, wherein the external stimulus is applied as short pulses of light, said pulses being of duration from 0.01 milliseconds to 10 seconds.

8. The method of claim 7, wherein the number of pulses are 1 to 100.

9. A method for identifying relative sensitivities of olfactory sensory neurons to an odorant comprising the steps of:
   a) providing a plurality of populations of OSNs, each OSN expressing an olfactory receptor (OR) and a permanent activity marker (PAM), wherein the PAM has been introduced into the OSN and exhibits a permanent and detectable change upon activation of the OSN in response to an odorant and exposure to an external stimulus, wherein the PAM comprises:
   an EosFP polypeptide, which includes a C-terminus portion comprising the sequence of SEQ ID NO:2 and an N-terminus portion comprising the sequence of SEQ ID NO:3;
   a calmodulin (CaM) polypeptide, comprising the sequence of SEQ ID NO:4; and
   a M13 polypeptide, comprising the sequence of SEQ ID NO:5 or a variant thereof, wherein the variant is a change in SEQ ID NO: 5 of:
      i) valine at position 13 to leucine, threonine, or aspartic acid,
      ii) tryptophan at position 6 to phenylalanine, leucine, or tyrosine,
      iii) glycine at position 10 to aspartic acid,
      iv) tryptophan at position 6 to phenylalanine and valine at position 13 to leucine,
      v) tryptophan at position 6 to tyrosine and valine at position 13 to threonine,
      vi) tryptophan at position 6 to phenylalanine and glycine at position 10 to aspartic acid; or
      vii) tryptophan at position 6 to phenylalanine and valine at position 13 to histidine;
   b) exposing each population of OSNs to a test odorant;
   c) exposing each population of OSNs to a pulse of external stimulus that will cause the PAM to exhibit the detectable change if the OSN containing the PAM has been activated in response to the odorant, wherein each population is exposed to a pulse of different length of time;
   d) isolating the OSNs exhibiting the detectable change in PAM from the OSNs that do not exhibit the detectable change in PAM for each population; and
   e) identifying the OR or ORs expressed in the isolated OSNs for each set; wherein the relative sensitivity of each OR can be determined based on the length of pulse needed for the expression of that OR.

10. The method of claim 9, wherein the different populations are from different individuals.

11. The method of claim 9, wherein the different populations are from the same individual.

12. The method of claim 9, wherein the detectable change in step b) is a color shift of a fluorescence emitted by the isolated polypeptide from green to red, an increase in brightness of the fluorescence, an increase in a red-to-green ratio of the fluorescence, or a combination thereof.

13. The method of claim 12, wherein the detectable change is normalized against the amount of light delivered to the cell.

* * * * *

UNITED STATES PATENT AND TRADEMARK OFFICE
CERTIFICATE OF CORRECTION

PATENT NO. : 10,041,935 B2
APPLICATION NO. : 14/451998
DATED : August 7, 2018
INVENTOR(S) : Rinberg et al.

Page 1 of 1

It is certified that error appears in the above-identified patent and that said Letters Patent is hereby corrected as shown below:

In the Specification

Column 2, Line 57, in part, should read:
--v0.1 has 20 fewer amino acid--

Signed and Sealed this
Thirtieth Day of October, 2018

Andrei Iancu
*Director of the United States Patent and Trademark Office*